(12) United States Patent
Studley et al.

(10) Patent No.: US 6,559,323 B1
(45) Date of Patent: May 6, 2003

(54) PROCESS FOR THE PREPARATION OF AN OXIRANE, AZIRIDINE OR CYCLOPROPANE

(75) Inventors: John Richard Studley, Abingdon (GB); Varinder Kumar Aggarwal, Sheffield (GB)

(73) Assignees: Avecia Limited, Manchester (GB); University of Sheffield, Sheffield (GB)

( * ) Notice: Subject to any disclaimer, the term of this patent is extended or adjusted under 35 U.S.C. 154(b) by 0 days.

(21) Appl. No.: 09/423,428

(22) PCT Filed: May 1, 1998

(86) PCT No.: PCT/GB98/01289

§ 371 (c)(1),
(2), (4) Date: Feb. 28, 2000

(87) PCT Pub. No.: WO98/51666

PCT Pub. Date: Nov. 19, 1998

(30) Foreign Application Priority Data

May 9, 1997 (GB) .............................................. 9709528

(51) Int. Cl.[7] .................... C07D 301/02; C07D 335/02; C07D 339/08; C07D 327/06; C07D 203/22
(52) U.S. Cl. ........................ 549/519; 436/903; 534/558; 548/966; 548/967; 548/968; 548/969; 585/377; 585/378
(58) Field of Search .......................... 549/519; 534/558; 436/903; 548/966, 967, 968, 969; 585/377, 378

(56) References Cited

FOREIGN PATENT DOCUMENTS

| WO | 95-11230 | 4/1995 |
|----|----------|--------|
| WO | WO 98/30569 | 7/1998 |

OTHER PUBLICATIONS

Jonczyk et al, Synthetic Communications, 8(8):569–572 (1978).
Jonczyk et al, Bull Soc. Chim. Belg., vol. 86(9):739–740.
Aggarwal, et al., "Novel Catalytic and Asymmetric Process for Aziridination Mediated by Sulfur Ylides" The Journal of Organic Chemistry, vol. 61, No. 24, XP002088745, 1996, pp. 8368–8369.
Aggarwal, et al., "Novel Catalytic Cycle for the Synthesis of Epoxides from Aldehydes and Sulfur Ylides Mediated by Catalytic Quantities of Sulfides and Rh2(OAc)4", Journal of the American Chemical Society, vol. 116, No. 13, XP002088746, 1994, pp. 5973–5974.
Toda, et al. "Ylide Reactions in the Solid State: a Simple Procedure for the Synthesis of Cyclopropanes, Oxiranes Aziridines", J. Chem. Soc. Perkin Trans. I, XP002088747, 1994, pp. 2673–2674.
Toshimitsu, et al., "Preparation of Chiral Aziridines from Chiral Oxiranes with Retention of Configuration", J. Chem. Soc. Chem. Commun., XP002088748, 1992, pp. 284–285.
Murray, et al., "Synthesis of Substituted 1,4 Oxathianes, . . . ", The Journal of Organic Chemistry, vol. 52, No. 4, XP002088749, 1987, pp. 525–529.
Kelstrup, "Preparation and Conformation of Some 4–Oxathinium Salts", J. Chem. Soc. Perkin I, XP002088750, 1979, pp. 1029–1036.
Deslongschamps, et al., 1,7–Dithia and 1–oxa–7–thiaspiro [5.5] undecanes . . . , Chemical Abstracts, vol. 95, No. 7, XP002088751, p. 643.

Primary Examiner—Ba K. Trinh
(74) Attorney, Agent, or Firm—Pillsbury Winthrop LLP

(57) ABSTRACT

A process for the preparation of an oxirane, aziridine or cyclopropane of formula (I),

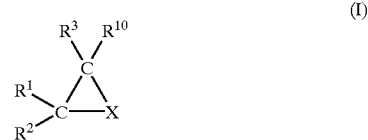

wherein X is oxygen, $NR^4$ or $CHR^5$; $R^1$ is hydrogen, alkyl, aryl, heteroaromatic, heterocyclic or cycloalkyl; $R^2$ is hydrogen, alkyl, aryl, heteroaromatic, $CO_2R^8$, $CHR^{14}NHR^{13}$, heterocyclic or cycloalkyl; or $R^1$ and $R^2$ join together to form a cycloalkyl ring; $R^3$ and $R^{10}$ are, independently, hydrogen, alkyl, aryl, heteroaromatic, $CO_2R^8$, $R^8{}_3Sn$, $CONR^8R^9$, trialkylsilyl or triarylsilyl; $R^4$ is an electron withdrawing group; $R^5$ is alkyl, cycloalkyl, aryl, heteroaromatic, $SO_2R^8$, $SO_3R^8$, $COR^8$, $CO_2R^8$, $CONR^8R^9$, $PO(R^8)_2$, $PO(OR^8)_2$ or CN; $R^8$ and $R^9$ are independently alkyl or aryl; and $R^{13}$ and $R^{14}$ are independently hydrogen, alkyl or aryl is provided. The process comprises degrading a compound of formula (II), (IIa), (IIb) or (IIc):

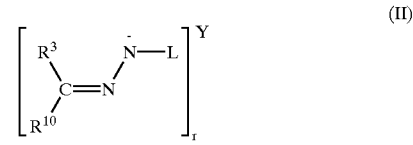

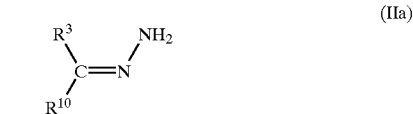

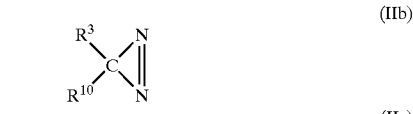

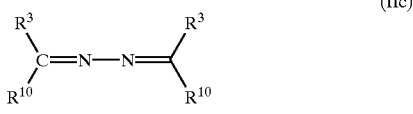

wherein $R^3$ and $R^{10}$ are as defined above; Y is a cation; depending on the nature of Y, r is 1 or 2; and L is a suitable leaving group, to form a diazo compound. The diazo compound is reacted with a suitable transition metal catalyst, and the product thereof reacted with a sulphide of formula $SR^6R^7$, wherein $R^6$ and $R^7$ are independently alkyl, aryl or heteroaromatic, or $R^6$ and $R^7$ join together to form an optionally substituted ring which optionally includes an additional heteroatom. This product is then reacted with an aldehyde, ketone, imine or alkene.

22 Claims, No Drawings

PROCESS FOR THE PREPARATION OF AN OXIRANE, AZIRIDINE OR CYCLOPROPANE

The present invention relates to a process for the preparation of oxiranes from aldehydes or ketones, of aziridines from imines, or of cyclopropanes from alkenes.

It is known from WO95/11230 to prepare oxiranes, aziridines and cyclopropanes by reacting a diazo compound with an aldehyde, ketone, imine or alkene as appropriate in the presence of both a sulphide and either an organometallic or an inorganic reagent to form a sulphur ylide. As diazo compounds are difficult to handle due to their toxicity and explosive nature it would be advantageous to generate the diazo compounds in situ for this process thereby minimising the handling of these hazardous materials.

Thus, according to one aspect of the present invention there is provided a process for the preparation of an oxirane, aziridine or cyclopropane of formula (I), wherein X is oxygen, $NR^4$ or $CHR^5$; $R^1$ is hydrogen, alkyl, aryl, heteroaromatic, heterocyclic or cycloalkyl; $R^2$ is hydrogen, alkyl, aryl, heteroaromatic, $CO_2R^8$, $CHR^{14}NHR^{13}$, heterocyclic or cycloalkyl; or $R^1$ and $R^2$ join together to form a cycloalkyl ring; $R^3$ and $R^{10}$ are, independently, hydrogen, alkyl, aryl, heteroaromatic, $CO_2R^8$, $R^8{}_3Sn$, $CONR^8R^9$, trialkylsilyl or triarylsilyl; $R^4$ is an electron withdrawing group; $R^5$ is alkyl, cycloalkyl, aryl, heteroaromatic, $SO_2R^8$, $SO_3R^8$, $COR^8$, $CO_2R^8$, $CONR^8R^9$, $PO(R^8)_2$, $PO(OR^8)_2$ or CN; $R^8$ and $R^9$ are independently alkyl or aryl; and $R^{13}$ and $R^{14}$ are independently hydrogen, alkyl or aryl; the process comprising the steps of:

(a) degrading a compound of formula (II), (IIa), (IIb) or (IIc), wherein $R^3$ and $R^{10}$ are as defined above; Y is a cation; depending on the nature of Y, r is 1 or 2; and L is a suitable leaving group, to form a diazo compound of formula (III) wherein $R^3$ and $R^{10}$ are as defined above;

(b) reacting the compound of formula (III) with a suitable transition metal catalyst (c) reacting the product of step (b) with a sulphide of formula $SR^6R^7$, wherein $R^6$ and $R^7$ are independently alkyl, aryl or heteroaromatic, or $R^6$ and $R^7$ join together to form an optionally substituted ring which optionally includes an additional heteroatom; and (d) reacting the product of step (c) with a compound of formula (IV) wherein $R^1$ and $R^2$ are as defined above.

When the compound of formula (IV) is an alkene (that is, when X in the compound of formula (IV) is $CHR^5$) it is an electron deficient alkene.

When the process of the present invention is used to prepare an oxirane (that is, a compound of formula (I) wherein X is O, it is necessary to balance the reactivity of the compound of formula (IV) against the reactivity of the product of step (c).

It is preferred that the compounds of formula (II) are degraded thermally (see, for example, Synth. Comm. 1978, 8(8) 569 or Bull. Soc. Chim. Belg. 1977, 86, 739); that the compounds of formula (IIa) are degraded by contacting the compounds with, for example, lead tetraacetate or manganese dioxide (see, for example, the procedure of Holton in J. Org. Chem. 1995, 60, 4725 and references cited therein); that the compounds of formula (IIb) are degraded thermally or by the action of light (hv) (see, for example, the procedure of Doyle in Tett. Lett. 1989, 30, 3049 and references cited therein); and that the compounds of formula (IIc) are degraded by thermal oxidation (see, for example, the procedure of Horner in Chem. Ber. 1961, 94, 279).

The process of the present invention can be carried out in the presence of a solvent. Suitable solvents include nitriles (such as acetonitrile), chlorinated solvents (such as $CH_2Cl_2$ or $CHCl_3$), aromatic solvents (such as benzene, toluene and o-, m- or p-xylene), aliphatic alcohols (such as methanol, ethanol or tert-butanol), chain or cyclic ethers (such as diethyl ether, tert-butyl methyl ether, diisopropyl ether, glymes (for example monoglyme, diglyme or triglyme) or tetrahydrofuran), aliphatic or alicyclic hydrocarbons (such as n-hexane or cyclohexane), N,N-dimethylformamide, sulpholane, dimethylsulphoxide or N-methylpyrrolidone.

Alternatively, the process can be carried out in a mixture of miscible solvents (such as a mixture of water and acetonitrile), or different reagents may be added in different solvents.

Phase transfer reagents can be used during the process of the present invention (for example when the process of the invention is carried out in a solvent and the reaction mixture is not homogenous). Suitable phase transfer reagents include ammonium salts (such as benzyltriethylammonium chloride) or crown ethers.

It is preferred that the process of the present invention is carried out at a temperature in the range −30 to 100° C., especially in the range 20 to 70° C., such as at about 50° C.

In preferred embodiments of the first aspect of the present invention, the compound of formula (II), (IIa), (IIb) or (IIc) is decomposed in the presence of the transition metal catalyst, the sulphide and the substrate compound of formula (IV).

According to a second aspect of the present invention, there is provided a process for the generation of diazo compounds, wherein a compound of formula II is thermally decomposed in the presence of an aprotic solvent and a phase transfer catalyst, but in the absence of free base.

In the process of the second aspect of the present invention, the aprotic solvent may comprise a nitrile (such as acetonitrile); a chlorinated solvent (such as $CH_2Cl_2$ or $CHCl_3$); an aromatic solvent (such as benzene, toluene and o-, m- or p-xylene); a chain or cyclic ether (such as diethyl ether, tert-butyl methyl ether, diisopropyl ether, a glyme (for example monoglyme, diglyme or triglyme) or tetrahydrofuran); an aliphatic or alicyclic hydrocarbon (such as n-hexane or cyclohexane); N,N-dimethylformamide; sulpholane; dimethylsulphoxide or N-methylpyrrolidone. Acetonitrile is particularly preferred. Most preferably, the process according to the second aspect is carried out under anhydrous conditions, ie in the substantial absence of water. Preferred phase transfer catalysts include quaternary ammonium salts, particularly trialkylbenzyl and tetraalkyl ammonium halides, especially chlorides, and most preferably those wherein each alkyl is independently a $C_{1-16}$ alkyl group. When the compound of formula II is a quaternary ammonium salt, the compound of formula II also serves as phase transfer catalyst. Most advantageously, the compound of formula II is substantially insoluble in the aprotic solvent, and is employed as a suspension. It is particularly preferred that the compound of formula II is a sodium salt. The thermal decomposition is often effected at a temperature of from 0 to 70° C., preferably from about 15 to about 50° C.

The compounds of formula (I) may have one, two or three chiral ring-carbon atoms and the process of the first aspect of the present invention is capable of forming all structural isomers of the compounds of formula (I). When one or more of $R^1$, $R^2$, $R^3$, $R^4$ or $R^5$ is chiral it can affect the stereochemical nature of the compound of formula (I) produced by the process of the present invention.

The term alkyl whenever it is used refers to straight or branched alkyl chains preferably containing from 1 to 10, especially from 1 to 6, for example from 1 to 4, carbon atoms. Alkyl is, for example, methyl, ethyl, n-propyl, n-butyl or tert-butyl. All alkyl groups are optionally substituted. Preferred substituents are one or more of aryl (such as phenyl), aryloxy (such as phenoxy), heteroaromatic, heterocyclic (such as reduced forms of oxazole), cycloalkyl (such as cyclopropyl), $C_{1-6}$ alkoxy (such as methoxy or ethoxy), $C_{1-6}$ thioalkyl (such as methylthio), halogen (to form, for example, $CCl_3$, $CF_3$ or $CH_2CF_3$), $C_{1-6}$ haloalkoxy (such as $OCF_3$), cyano, hydroxy or $CO_2(C_{1-6})$alkyl. In addition the alkyl groups of $R^5$ may terminate with an aldehyde (C(H)=O) group or be interrupted with a carbonyl (C=O) group.

Halogen is fluorine, chlorine, bromine or iodine.

Alkoxy and haloalkoxy groups are straight or branched chains, preferably containing from 1 to 4 carbon atoms.

Haloalkoxy and haloalkyl groups do not have a halogen that is susceptible to nucleophilic substitution. Thus, a carbon atom of a haloalkyl or haloalkoxy group must not carry a halogen atom and a hydrogen atom.

Cycloalkyl rings contain, preferably from 3 to 7, especially from 3 to 6 carbon atoms. Cycloalkyl rings, can be substituted by one or more alkyl groups, $CO_2R^8$ (wherein $R^8$ is as defined above) or two ring carbons may be joined to each other by a carbon chain containing from 1 to 4 (preferably 1 or 2) carbon atoms to form a bicyclic structure.

Aryl includes naphthyl but is preferably phenyl.

Heteroaromatic includes 5- and 6-membered aromatic rings containing one, two, three or four heteroatoms selected from the list comprising oxygen, sulphur and nitrogen and can be fused to benzenoid ring systems. Examples of heteroaromatic rings are pyridyl, pyrimidyl, pyridazinyl, pyrazinyl, triazinyl (1,2,3-, 1,2,4- and 1,3,5-), furyl, thienyl, pyrrolyl, pyrazolyl, imidazolyl, triazolyl (1,2,3- and 1,2,4-), tetrazolyl, oxazolyl, isoxazolyl, thiazolyl, isothiazolyl, quinolinyl, isoquinolinyl, cinnolinyl, quinazolinyl, quinoxalinyl, indolinyl, isoindolinyl, benzofuranyl, benzothienyl, benzimidazolyl, benzoxazole, benzthiazole, oxadiazole and thiadiazole.

All aryl and heteroaromatic groups are optionally substituted. Preferred substituents include one or more of alkyl, haloalkyl, $C_{1-6}$ alkoxy, halogen, $C_{1-6}$ haloalkoxy, cycloalkyl, nitro, cyano or $CO_2(C_{1-6})$alkyl.

Heterocyclic is used in relation to non-aromatic rings and includes include 5- and 6-membered rings containing one, two or three heteroatoms selected from the group comprising oxygen, sulphur and nitrogen. Examples are piperidine, pyrrolidine, azetidine, morpholine, tetrahydrofuran, tetrahydrothiophene, pyrroline, piperazine, isoxazoline, oxazoline and reduced forms of heteroaromatics not previously mentioned. Heterocyclic rings are optionally substituted and preferred substituents include one or more alkyl groups.

When the compound of formula (IV) is an aldheyde, $R^2$ is preferably an optionally substituted alkyl group comprising from 1 to 10 carbon atoms; an optionally substituted phenyl group, particularly substituted at one or both of the positions ortho or para to the aldehyde moiety or an optionally substituted heteroaromatic group comprising a 5 or 6 membered ring, especially comprising 1,2 or 3 nitrogen heteroatoms.

When the compound of formula (IV) is a ketone, at least one of $R^1$ and $R^2$ often represents an optionally substituted alkyl group comprising from 1 to 10 carbon atoms, or forms a cycloalkyl group, and most often the carbon alpha to the keto group carries one, and preferably two hydrogen atoms. When one or both, preferably one, of $R^1$ and $R^2$ represents an aryl or heteroaromatic group, the ring positions adjacent to the keto group preferably carry hydrogen atoms. Aliphatic ketones, particularly those comprising up to 16 carbon atoms are most preferred.

When the compound of formula (IV) is an alkene, it is preferred that the alkene is conjugated with an electron withdrawing group, preferably a carbonyl, nitro, cyano phosphoryl or sulphonyl group, especially a group of formula $SO_2R^8$, $SO_3R^8$, $COR^8$, $CO_2R^8$, $CONR^8R^9$, CN, $P(O)(R^8)_2$, especially $P(O)(aryl)_2$ or $PO(OR^8)_2$; wherein $R^8$ and $R^9$ are as defined above. When $R^8$ or $R^9$ comprises an alkyl group, it is preferably a $C_{1-6}$ alkyl group, which may be substituted. When $R^8$ or $R^9$ comprises an aryl group, it is preferably a phenyl group, which may be substituted.

When the compound of formula (IV) is an imine, it is preferred that one of $R^1$ and $R^2$ represents H, alkyl, phenyl or a heteroaromatic group, the other representing alkyl, aryl or a heteroaromatic group, wherein any alkyl group preferably comprises from 1 to 10 carbon atoms; and is optionally substituted; any phenyl group is optionally substituted, particularly at one or both of the positions ortho or para to the aldehyde moiety and any heteroaromatic group comprises a 5 or 6 membered ring, especially comprising 1,2 or 3 nitrogen heteroatoms, and is optionally substituted. $R^4$ is an electron withdrawing group, such as a group of formula $SO_2R^8$, $SO_3R^8$, $COR^8$, $CO_2R^8$, $CONR^8R^9$, CN, $P(O)(R^8)_2$, especially $P(O)(aryl)_2$ or $PO(OR^8)_2$; wherein $R^8$ and $R^9$ are as defined above. When $R^8$ or $R^9$ comprises an alkyl group, it is preferably a $C_{1-6}$ alkyl group, which may be substituted. When $R^8$ or $R^9$ comprises an aryl group, it is preferably a phenyl group, which may be substituted.

In the sulphides which are employed in the process of the first aspect of the present invention, it is preferred that at least one of $R^6$ and $R^7$ represents an alkyl group. In many embodiments, the sulphide is an aliphatic sulphide.

Examples of sulphides that can be employed include those compounds listed as structures (A) to (AB) below.

The ring formed when $R^6$ and $R^7$ join preferably contains from 1 to 12 (for example from 2 to 10, especially from 2 to 6 [see, for example, (B), (C) or (C')]) carbon atoms, optionally includes an additional heteroatom (preferably a nitrogen, oxygen or sulphur atom) [see, for example, (D) or (J)] and is optionally substituted. This ring may be fused to other rings (for example aryl [such as naphthyl, see, for example, (A)] or mono- or bi-cyclic carbon ring systems (such as cyclohexane [see, for example, (F), (G), (K) or (L)] or camphor [see, for example, (D) or (J)]) which are optionally substituted (for example substituted with alkyl, aryl or heteroaryl). When the cyclic sulphide is a 1,3-oxathiane, the 2-position is preferably unsubstituted or carries one substituent wherein the carbon alpha to the 2-position carries at least one, and preferably at least two hydrogen atoms, and particularly such substituents are primary or secondary alkyl groups. The ring may also incorporate carbon-carbon double bonds, and when such a double bond is present, there is preferably only one such bond in the ring also comprising the S atom. Cyclic sulphides may also be substituted by an alkenyl group, and, when present, such an alkenyl substituent particularly substitutes a ring fused to the ring comprising the sulphur atom.

A particular class of cyclic sulphides which can be employed in the process of the present invention has the general chemical formula (VI):

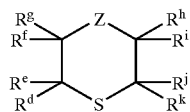

wherein Z represents —CH$_2$—, O, S, —CHalkyl-, C(alkyl)$_2$— or NR$^4$, each of R$^{d-k}$ independently represents H, alkyl or alkoxyalkyl or are linked to form a cyclic moiety, provided that at least 2 of R$^d$, R$^e$, R$^j$ and R$^k$ represent H, and R$^4$ is as hereinbefore defined. Advantageously, the nature of R$^{d-k}$ is selected such that the sulphide is chiral.

In certain embodiments, two of R$^{d-k}$ can be linked so as to form a bridging group, for example comprising 1 to 4 bridging atoms, or a fused cyclic group, for example forming a 5 or preferably 6, membered ring. In certain preferred embodiments, either R$^d$ and R$^e$ or R$^j$ and R$^k$ are linked to form a cyclic group, preferably forming a 5-, or especially a 6-membered ring.

The compounds of formula (VI) where either R$^d$ and R$^e$ or R$^j$ and R$^k$ are linked to form a cyclic group are novel and form an aspect of the present invention.

The compounds of formula (VI) wherein Z represents O, and the nature of the groups R$^{d-k}$ are such that the compounds are chiral are novel and form an aspect of the present invention. In certain preferred compounds of formula (VI), one of R$^d$ and R$^e$ and one of R$^f$ and R$^g$, or one of R$^h$ and R$^i$ and one of R$^j$ and R$^k$ are linked to form a six membered ring. In other preferred compounds of formula (VI), both of R$^f$ and R$^g$ and one of R$^d$ and R$^e$ are independently alkyl, especially C$_{1-6}$ Alkyl or alkoxyalkyl, especially C$_{1-4}$alkoxyC$_{1-6}$alkyl, with the remainder of R$^{d-k}$ representing hydrogen.

A further class of sulphides which may be employed in the process of the present invention have the chemical formula (VII)

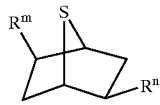

wherein R$^m$ and R$^n$ are each independently alkyl, especially C$_{1-6}$ alkyl or alkoxyalkyl, especially C$_{1-4}$alkoxyC$_{1-6}$alkyl.

Alternatively, the sulphide of formula SR$^6$R$^7$ may be a bis-sulphide (such as (E)) or may be incorporated into the molecular structure of the organometallic compound (such as (H)).

The substituents referred to in structures (A)–(AB) are defined as follows: R', R" and R"' are, independently, hydrogen, alkyl, alkoxyalkyl, aryl or heteroaryl, and are particularly hydrogen, C$_{1-6}$ alkyl or C$_{1-4}$alkoxyC$_{1-6}$alkyl; in (F), (G), (L) and (O) R' and R" may join to form a 3 to 8-membered carbocyclic ring optionally substituted with alkyl; in (D), R$^a$ is hydrogen or primary or secondary unsubstituted, mono- or di-substituted alkyl, and R$^b$ is hydrogen, alkyl, aryl or heteroaryl; R$^a$ may also be CH$_2$O(CH$_2$)$_n$O(CH$_2$)$_m$OR$^b$ or (CH$_2$)$_p$CO(CH$_2$)COR$^b$; or alternatively R$^a$ is linked to a polymer support; wherein n, m and p are integers (preferably 1–10); in (E), R$^c$ is (Q) or (CH$_2$)$_q$Sr'; R$^{22}$ is hydrogen, alkyl or trialkylsilyl; and R$^{23}$ is hydrogen or alkyl; wherein q is an integer of 2 or more (preferably 2–10). It is preferred that R$^b$ is hydrogen.

The groups R$^a$ and R$^b$ in structure (D) are, for example:

| R$^a$ | R$^b$ |
|---|---|
| CH$_3$ | H |
| (CH$_3$)$_2$CH | H |
| CH$_2$OCH$_3$ | H |
| CH$_2$O(CH$_2$)$_3$CH$_3$ | H |
| CH$_3$(CH$_2$)$_3$ | H |
| CH$_2$OC$_6$H$_5$ | H |
| CH$_3$ | CH$_3$ |
| CH$_3$(CH$_2$)$_2$ | CH$_3$(CH$_2$)$_2$ |
| CH$_2$OH | H |
| CH$_2$O(CO)CH$_3$ | H |
| CH$_2$O(CO)(4-NO$_2$—C$_6$H$_4$) | H |
| CH$_2$CN | H |

In structures (P), (R), (S), (T), (U), (V), (W), (X), (Y), (Z), (AA) and (AB), the methyl and iso-propyl groups, particularly those methyl groups substituting the ring comprising the S atom, may be replaced by an alternative alkyl group, preferably a C$_{1-6}$ alkyl group, most preferably a C$_{1-4}$ alkyl group, or by an alkoxyalkyl group, preferably a C$_{1-4}$alkoxyC$_{1-6}$alkyl group, most preferably a C$_{1-4}$ alkoxymethyl group.

Suitable transition metal catalysts are those which convert diazo compounds to carbenes, and include particularly rhodium, ruthenium, copper, nickel and palladium compounds, and especially complexes. When the transition metal catalyst comprises a rhodium compound, it is commonly a rhodium (0) or rhodium (II) compound, and preferably rhodium (II). When the transition metal catalyst comprises a ruthenium compound, it is commonly a ruthenium (0), (II) or (III) compound, and preferably a ruthenium (II) compound. When the transition metal catalyst comprises a copper compound, it is commonly a copper (0), (I) or (II) compound, including metallic Cu, and preferably a Cu(I) or (II) compound. When the transition metal catalyst comprises a nickel compound, it is commonly a nickel (0) or (II) compound, and preferably a nickel (II) compound. When the transition metal catalyst comprises a palladium compound, it is commonly a palladium (0) or palladium (II) compound, and preferably a palladium (II) compound.

Suitable transition metal catalysts preferably comprise rhodium or ruthenium. Suitable reagents include Rh$_2$(OCOR.)$_4$ or Ru$_2$(OCOR.)$_4$ [wherein R. is hydrogen, alkyl (preferably methyl), C$_{1-4}$ perfluoroalkyl (such as trifluoromethyl, 2,2,2-trifluoroethyl or pentafluoroethyl), aryl, (CHOH)alkyl or (CHOH)aryl], such as Rh$_2$(OCOCH$_3$)$_4$ or Rh$_2$(OCOCF$_3$)$_4$; or can be RuCl$_2$(P(C$_6$H$_5$)$_3$)$_2$, RuCl(H$_2$C$_2$B$_9$H$_{10}$)(P(C$_6$H$_5$)$_3$)$_2$ or RH$_6$(CO)$_{16}$.

Alternatively, suitable transition metals comprise copper, nickel or palladium. Examples of suitable reagents include CuBr, CuCl, CuOSO$_2$CF$_3$, CuBr$_2$, CuCl$_2$, CuSO$_4$, Cu(CH$_3$CO$_2$)$_2$ a copper compound of formula (V) (wherein R$^{20}$ and R$^{21}$ are both methyl [that is, Cu(acetylacetonate)$_2$], phenyl or tert-butyl, or R$^{20}$ is phenyl and R$^{21}$ is methyl), [Cu(CH$_3$CN)$_4$]BF$_4$, NiBr$_2$, NiCl$_2$, NiSO$_4$, Cu(CH$_3$CO$_2$)$_2$, the nickel analogue of the compound of formula (V) (wherein R$^{20}$ and R$^{21}$ are both methyl [that is, Ni(acetylacetonate)$_2$], phenyl or tert-butyl, or R$^{20}$ is phenyl and R$^{21}$ is methyl), Pd(OCOCH$_3$)$_2$, Pd(acetylacetonate)$_2$, Pd(CH$_3$CN)$_2$Cl$_2$ or Pd(C$_6$H$_5$CN)$_2$Cl$_2$.

Suitable cations (Y) for compounds of formula (II) are cations of alkali metals (especially sodium, potassium or lithium), cations of alkaline earth metals (such as magnesium or calcium) or quaternary ammonium salts [such as (C$_{1-6}$ alkyl)$_4$N$^+$, wherein the alkyl group is unsubstituted, for example $(CH_3(CH_2)_3)_4N^+]$. It is preferred that Y is the cation of sodium (that is, $Na^+$).

Suitable leaving groups (L) for compounds of formula (II) include arylsulphonyl (that is $arylSO_2$) compounds (wherein the aryl is mono-, di- or tri-substituted with unsubstituted $C_{1-10}$ alkyl or is monosubstituted with nitro) or unsubstituted $C_{1-10}$ alkylsulphonyl compounds. Examples of suitable leaving groups are p-tosyl, 2,4,6-tri-iso-propylphenylsulphonyl, 2-nitrophenylsulphonyl and mesyl.

The compounds of formula (II) can be prepared by adaptation of methods found in the literature. For example, the compounds wherein L is tosyl can be prepared from tosyl hydrazones by adapting the methods of Creary (Organic Synth. 1986, 64, 207), Bertz (J. Org. Chem. 1983, 48, 116) or Farnum (J. Org. Chem. 1963, 28, 870). Tosyl hydrazones can be prepared from tosyl hydrazides which can in turn be prepared by reacting tosyl hydrazine with an aldehyde of formula $R^3CHO$.

In many embodiments, only one, or neither, of $R^3$ and $R^{10}$ represents hydrogen. Preferably one of $R^3$ or $R^{10}$ is an alkyl, aryl or amide group. When one of $R^3$ or $R^{10}$ represents a group of formula $—CONR^8R^9$, especially when X is O, it is preferred that the sulphide employed is not a 1,3-oxathiane.

It is preferred that the nucleophilicity of the sulphide of formula $SR^6R^7$ is such that the rate of reaction of the product of step (b) with the sulphide of formula $SR^6R^7$ is greater than the rate of reaction of the product of step (b) with the compound of formula (III).

It is possible to influence the stereochemistry of the compound of formula (I) produced by the process. This can be done by using a chiral sulphide of formula $SR^6R^7$ (such as structures (C'), (D), (F), (G), (H), (J), (K) or (L), (M), (N), (O), (O"), (P), and (R) to (AB)). The relative amounts of the stereochemical products will depend on the nature of the chiral sulphide used. Thus, in a further aspect the present invention provides a process as hereinbefore described wherein a chiral sulphide is used.

In another aspect the present invention provides a process as previously described wherein the organometallic reagent is present in a less than stoichiometric amount (such as from 0.5 to 0.001, for example from 0.015 to 0.005, equivalents).

In a further aspect the present invention provides a process as previously described wherein a less than a stoichiometric amount of sulphide is used in relation to the amount of compound of formula (IV). For example it is preferred that the amount of sulphide used is in the range 1.00–0.01 equivalents (such as in the range 0.75–0.02 (for example 0.5–0.05 (particularly about 0.2)) equivalents).

In a further aspect the present invention provides a process as hereinbefore described wherein a chiral sulphide is used in an amount in the range of 0.5–0.1 equivalents relative to the amount of compound of formula (IV) used.

In a still further aspect the present invention provides a process as hereinbefore described wherein the compound of formula (IV) is an aldehyde, ketone, imine or alkene.

In another aspect the present invention provides a process as defined above wherein X is oxygen.

In a further aspect the present invention provides a process for preparing a compound of formula (I) wherein X is oxygen and $R^1$ is hydrogen, and the process is conducted under the following conditions:

| | |
|---|---|
| Compound of formula (IV) wherein $R^1$ is hydrogen | 1 equivalent |
| Rhodium Acetate | 1 mol % |
| Compound of formula (II) | 1.5 equivalents |
| Benzyltriethyl-ammonium Chloride | 20 mol % |
| Tetrahydrothiophene | 20 mol % |
| Acetonitrile | 3 cm³/mmol compound of formula (IV) wherein $R^1$ is hydrogen |
| Temp/Time | 40–45° C./3–5 hours |

In a still further aspect the present invention provides a process for preparing a compound of formula (I) wherein X is oxygen, wherein: a compound of formula (II) (wherein Y is $Na^+$) is used in step (a) and this compound is degraded in situ at low temperature for extended reaction times (typically 30° C. for 32 hours) and acetonitrile is used as solvent. In another aspect the sulphide of formula $R^6R^7$ is used in 100 mol %.

In a further aspect the present invention provides a process as hereinbefore described wherein a compound of formula (II) is used in step (a). In another aspect the present invention provides a process as hereinbefore described wherein and using a compound of formula (II) in step (a) wherein the compound of formula (II) is prepared from the corresponding hydrazone (that having been prepared by contacting the corresponding aldehyde or ketone with a suitable hydrazide).

In a still further aspect the present invention provides a process for the preparation of a compound of formula (I), the process comprising:

1. adding a compound of formula (II) to a mixture of:
   a compound of formula (IV),
   a sulphide of formula $SR^6R^7$ and
   either a rhodium compound of formula $Rh_2(OCOR.)_4$ (wherein R. is preferably methyl) or a copper (II) acetoacetonate,
   a solvent (preferably acetonitrile or a mixture of acetonitrile and water) and, optionally,
   a phase transfer catalyst (preferably benzyltriethylammonium chloride);
2. heating the resulting mixture to a temperature in the range 20–60° C. for a time period (preferably 1–48 hours); and
3. extracting the compound of formula (I) from the mixture so formed.

The following Examples illustrate the invention. The following abbreviations are used throughout the Examples:

| | | |
|---|---|---|
| m = multiplet | s = singlet | d = doublet |
| dt = doublet of triplets | brs = broad singlet | dd = doublet of doublets |
| brd = broad doublet | EtOAc = ethyl acetate | tosyl = p-toluenesulphonyl |

All solvents used in reactions were distilled prior to use. Tetrahydrofuran (THF) and diethyl ether were freshly distilled from sodium under an atmosphere of dry nitrogen using benzophenone as an indicator. Acetonitrile and dichloromethane (DCM) were freshly distilled from calcium hydride. Reagents were either used as received from commercial sources or purified by recognised methods. Petroleum ether (petrol) refers to that fraction which boils in the range 40–65° C. Liquid aldehydes were distilled prior to use, either neat or from calcium sulphate. Copper (II) acetylacetonate was sublimed prior to use.

All reactions, unless otherwise stated, were carried out in oven dried glassware under an atmosphere of dry nitrogen or argon.

Flash chromatography was performed using Kieselgel 60 F254 and on C560, 40–63 micron silica gel. All reactions were monitored by thin layer chromatography (TLC) carried out on aluminium sheets precoated with 60F$_{254}$ silica gel, unless otherwise stated, and were visualised by UV light at 254 nm, then potassium permanganate solution, phosphomolybdic acid (PMA) solution or anisaldehyde solution (epoxides appeared to stain very intensely with PMA solution).

$^1$H-NMR were recorded on a Bruker ACF-250 spectrometer operating at 250.13 MHz or a Bruker WH400 instrument operating at 399.7 MHz. The observed spectra were for solutions in deuterochloroform unless otherwise stated. The chemical shifts (d) were recorded in parts per million (ppm) relative to tetramethylsilane as an internal standard; all coupling constants, J, are reported in Hz.

$^{13}$C-NMR spectra were recorded on a Bruker ACF-250 spectrometer operating at 62.9 MHz. The spectra were recorded for solutions in deuterochloroform unless otherwise stated. The chemical shift (d) were recorded relative to deuteriochloroform (or relative solvent peak) as internal standard in a broad band decoupled mode; the multiplicities were obtained by using 135° and 90° "Distortionless Enhancement by Polarisation Transfer" (DEPT) or Off Resonance Decoupling experiments to aid in assignments (q, methyl; t, methylene; d, methine; s, quaternary).

Infra red spectra were recorded on a Perkin-Elmer 157G FT-IR, either as liquid films between sodium chloride plates or as KBr discs.

Mass spectra were recorded on a Kratos MS 25 or MS 80 instrument with a DS 55 data system using either an ionising potential of 70 eV (EI), or by chemical ionisation (isobutane) (CI) or fast atom bombardment (FAB) in 3NBA matrix.

Melting points (m.p.) were recorded on a Kofler Hot Stage Micro Melting Point Apparatus and are uncorrected.

Optical rotations were recorded on a Perkin-Elmer 141 Polarimeter at ambient temperature. [a] values are reported as $10^{-1}$ deg cm$^2$ g$^{-1}$. Microanalysis was carried out on a Perkin-Elmer 2400 Elemental Analyser.

High pressure liquid chromatography (HPLC) analysis, used to determine enantiomeric excesses, was carried out using a Gilson 303 HPLC pump, Waters 994 Tuneable Absorbance Detector or a Waters 2200 Data Module (analysis conditions are given below).

Diastereomeric ratios were determined by NMR analysis.

Preparation of Aryl Tosyl Hydrazones

Aryl tosyl hydrazones were prepared according to the method of Creary (Organic Synth. 1986, 64, 207).

To a rapidly stirred suspension of p-toluenesulphonyl hydrazide (5.0 g, 26.8 mmol) in methanol (10 cm$^3$) was added an aldehyde (24 mmol) dropwise (solid aldehydes were added as a methanol solution or portionwise). A mildly exothermic reaction ensued and the hydrazide dissolved. Within 5–10 minutes the tosyl hydrazone began to precipitate. After approximately 30 minutes the mixture was cooled to 0° C. and the product removed by filtration, washed with a small quantity of methanol and then recrystallised from hot methanol.

Benzaldehyde tosyl hydrazone: Isolated as white needles (5.40 g, 82%), m.p. 127–128° C.; dH 2.37 (3H,s), 7.26–7.37 (5H,m), 7.52–7.61 (2H,m), 7.80 (1H,s), 7.89 (2H,d, J 9), 8.44 (1H, brs).

4-Methylbenzaldehyde tosyl hydrazone: Isolated as white needles (6.22 g, 90%), m.p. 144–146° C.; (found C, 62.48; H, 5.52; N, 9.85. $C_{15}H_{16}N_2SO_2$ requires C, 62.5; H, 5.5; N, 9.7%); u$_{max}$ (KBr disc)/cm$^{-1}$ 3215, 1165, 1049, 814; d$_H$ 2.32 (3H,s), 2.37 (3H,s), 7.14 (2H,d, J 8), 7.31 (2H,d, J 8), 7.45 (2H,d, J 8), 7.75 (1H,s), 7.88 (2H, d, J 8.2), 8.19 (1H,brs); d$_C$ 21.5 (q), 21.6 (q), 127.4 (d), 127.9 (d), 129.4 (d), 129.7 (d), 130.5 (s), 135.3 (s), 140.8 (s), 144.2 (s), 148.3 (d); m/z (EI) 288 (M$^+$, 63%), 133 (63), 104 (100), 91 (41), 77 (25).

4-Chlorobenzaldehyde tosyl hydrazone: Isolated as colourless needles (6.74 g, 91%), m.p. 146–148° C.; (Found C, 54.27; H, 4.14; N, 9.21. $C_{14}H_{13}N_2SO_2Cl$ requires C, 54.5; H, 4.4; N, 9.1%); u$_{max}$ (KBr disc)/cm$^{-1}$ 3187, 1332, 1332, 1169; d$_H$ 2.41 (3H,s), 7.30–7.35 (4H,m), 7.49 (2H,d, J 7.8), 7.75 (1H,s), 7.87 (2H,d, J 7.8), 8.42 (1H,brs); d$_C$ 21.6 (q), 127.9 (d), 128.4 (d), 128.9 (d), 129.8 (d), 131.7 (s), 135.1 (s), 136.3 (s), 144.5 (s), 146.5 (d); m/z (EI) 308 (M$^+$, 49%), 152 (38), 124 (100), 89, (100), 63 (32).

3-Nitrobenzaldehyde tosyl hydrazone: Isolated as pale yellow needles (5.59 g, 73%), m.p. 154–156° C.; (Found C, 52.72; H, 3.99; N, 13.21. $C_{14}H_{13}N_3O_4S$ requires C, 52.7; H, 4.1; N,13.2%); u$_{max}$ (KBr disc)/cm$^{-1}$ 3218, 1533, 1349, 1166, 819; d$_H$ 2.43 (3H,s), 7.35 (2H,d, J 9), 7.55 (1H,dd, J 9, 6), 7.85–7.97 (4H,m), 8.18 (1H,dd, J 9, 5.8), 8.35 (1H,s), 8.54 (1H,brs); d$_C$ 21.7 (q), 122.0 (d), 124.7 (d), 128.0 (d), 129.8 (d), 129.9 (d), 132.6 (d), 134.9 (s), 135.0 (s), 144.4 (d), 144.8 (s), 148.5 (s); m/z (EI) 319 (M$^+$, 54%), 314 (30), 280 (85), 216 (78), 188 (50), 141 (48), 111 (42), 91 (38), 77 (100).

4-Methoxybenzaldehyde tosyl hydrazone: Isolated as white crystals, (6.10 g, 83%), m.p. 103–105° C.; (Found C, 59.24; H, 5.16; N, 9.17. $C_{15}H_{16}N_2O_3S$ requires C, 59.2; H, 5.3; N, 9.2%); u$_{max}$ (KBr disc)/cm$^{-1}$ 3222, 1161, 1044; d$_H$ 2.35 (3H,s), 3.75 (3H,s), 6.81 (2H,d, J 10.8), 7.25 (2H,d, J 8.1), 7.48 (2H,d, J 10.8), 7.74 (1H,s), 7.88 (2H,d, J 8.2), 8.55 (1H,brs); d$_C$ 21.6 (q), 55.4 (q), 114.1 (d), 126.0 (s), 127.9 (d), 128.9 (d), 129.7 (d), 135.3 (s), 144.2 (s), 148.4 (d), 161.4 (s); m/z (EI) 304 (M$^+$, 57%), 149 (94), 139 (43), 135 (60), 121 (100), 91 (90), 77 (48).

4-Cyanobenzaldehyde tosyl hydrazone: Isolated as pale yellow crystals (5.95 g, 83%), m.p. 161–164° C.; (Found C, 60.22; H, 4.34; N, 14.06. $C_{15}H_{13}N_3O_2S$ requires C, 60.2; H, 4.3; N, 14.0%); u$_{max}$ (KBr disc)/cm$^{-1}$ 3170, 2230, 1171; d$_H$ 2.40 (3H,s), 7.32 (2H,d, J 8), 7.64 (4H,m), 7.80 (1H,s), 7.88 (2H,d, J 8), 8.87 (1H,brs); d$_C$ 21.7 (q), 113.4 (s), 118.4 (s), 127.6 (d), 127.9 (d), 129.9 (d), 132.4 (d), 134.9 (s), 137.4 (s), 144.8 (s), 144.9 (d); m/z (EI) 299 (M$^+$, 6%), 156 (27), 143 (28), 115 (100), 91 (57), 65 (36).

2,4,6-Trimethylbenzaldehyde tosyl hydrazone: Isolated as white needles (5.69 g, 75%), m.p. 159–161° C.; (Found C, 64.47; H, 6.38; N, 8.89; S, 10.06. $C_{17}H_{20}N_2O_2S$ requires C, 64.5; H, 6.3; N, 8.9; S, 10.1%); u$_{max}$ (KBr disc)/cm$^{-1}$ 3203, 1608, 1557, 1326, 1165; d$_H$ 1.95 (3H,s), 2.25 (6H,m), 2.41 (3H,m), 6.84 (2H,m), 7.25–7.35 (2H,m), 7.55 (1H,brd), 7.80 (2H,m); d$_C$ 21.1 (q), 21.3(q), 21.6(q), 127.1 (s), 128.1 (d), 129.6(d), 135.3(s), 137.9 (s), 139.3 (s), 144.2 (s), 148.0 (d); m/z (EI) 316 (M$^+$, 37%), 161 (100), 132 (96), 91 (77).

Preparation of Alkyl Tosyl Hydrazones

Tosyl hydrazones of aliphatic aldehydes were prepared according to the method of Bertz (J. Org. Chem. 1983, 48, 116).

Pivaldehyde Tosyl Hydrazone p-Toluenesulphonyl hydrazide (3.24 g, 17.4 mmol) was added to 35 cm$^3$ of THF. The mixture was stirred vigorously and then filtered to remove insoluble material (ca. 100 mg). To the resulting solution was added pivaldehyde (1.92 cm$^3$, 17.4 mmol) dropwise. The mixture was then stirred magnetically for 1 hour after which time TLC indicated the reaction was complete. The THF was then removed under reduced pressure to give a white solid which was purified by recrystallisation from diethyl ether. The product was isolated as a white solid (2.31 g). Concentration of the filtrate gave a second crop (0.52 g, total yield 64%); m.p. 110–112° C.; $u_{max}$ (KBr disc)/cm$^{-1}$ 3199, 1327, 1166; $d_H$ 0.98 (9H,s), 2.42 (3H,s), 7.07 (1H,s), 7.28 (2H,d, J 8), 7.80–7.82 (3H,m); $d_C$ 21.6 (q), 27.1 (q), 35.1 (s), 128.3 (d), 129.4 (d), 135.0 (s), 144.0 (s), 160.2 (d); m/z (EI) 254 (M$^+$, 8%), 157 (36), 139 (25), 91 (100), 65 (48), 55 (97).

Preparation of Ketone-derived Tosyl Hydrazones

Aryl alkyl tosyl hydrazones were prepared by modification of the method of Farnum (J. Org. Chem. 1963, 28, 870).

Acetophenone Tosyl Hydrazone

A suspension of p-toluenesulphonyl hydrazide (3.11 g, 16.7 mmol) in glacial acetic acid (4 cm$^3$) was heated to 65° C. and stirred until all of the solid had dissolved. Acetophenone (1.94 cm$^3$, 16.7 mmol) was then added in one portion and heating continued until precipitation of the hydrazone occurred (approximately 5 minutes). The mixture was then cooled and the product removed by filtration. The pale yellow solid was washed with cold acetic acid, cold aqueous acetic acid then water. It was then air dried. The crude material was purified by recrystallisation from hot methanol. The hydrazone was obtained as a white solid (3.30 g, 69%); m.p. 130–132° C. (decomp.); (Found C, 62.24; H, 5.47; N, 9.82. $C_{15}H_{16}N_2O_2S$ requires C, 62.5; H, 5.6; N, 9.7%) $u_{max}$ (KBr disc)/cm$^{-1}$ 3223, 1166, 1050, 919; $d_H$ 2.19 (3H,s), 2.42 (3H,s), 7.28 (5H,m), 7.63 (2H,m), 7.96 (2H,m), 8.07 (1H, brs); $d_C$ 13.4 (q), 21.6 (q), 126.3 (d), 127.9 (d), 128.1 (d), 128.3 (d), 129.6 (d), 135.4 (s), 137.3 (s), 144.1 (s), 152.6 (s); m/z (EI) 288 (M$^+$, 43%), 133 (100), 104 (85), 92 (63), 77 (32), 65 (31).

Preparation of Tosyl Hydrazone Sodium Salts

Tosyl Hydrazone salts were prepared according to the method of Creary (Organic Synth. 1986, 64, 207).

A 1M sodium methoxide solution was prepared by adding sodium (288 mg, 12.5 mmol) to anhydrous methanol (12.5 cm$^3$) with external cooling. Once all of the metal had dissolved a tosyl hydrazone (12.35 mmol) was added and the mixture stirred until all of the solid had dissolved. (The sodium salts of tosyl hydrazones derived from 4-methylbenzaldehyde and 3-nitrobenzaldehyde precipitated from methanol and were filtered, washed and dried under vacuum.) After stirring for a further 15 minutes the methanol was removed under reduced pressure (at room temperature). The last traces of methanol were removed under high vacuum. The solid hydrazone salt was then ground to give a free flowing powder using a mortar and pestle.

Tosyl hydrazone sodium salts are best stored in a cool place in the absence of direct light.

Benzaldehyde tosyl hydrazone sodium salt: Isolated as a white solid, (Found C, 56.78; H, 4.34; N, 9.22. $C_{14}H_{13}N_2SO_2Na$ requires C, 56.8; H, 4.4; N, 9.5%); $u_{max}$ (KBr disc)/cm$^{-1}$ 3056, 1245, 1129, 1088,1054, 1037; $d_H$ ($D_2O$) 2.26 (3H,s), 7.29 (5H,m), 7.49 (2H,d, J 10), 7.71 (2H,d, J 10), 7.96 (1H,s); $d_C$ ($D_2O$) 20.39 (q), 126.2 (d), 126.5 (d), 128.5 (d), 129.2 (d), 135.6 (s), 139.2 (s), 142.3 (s), 145.5 (d); m/z (FAB) 297 (M$^+$+1, 84%).

4-Methylbenzaldehyde tosyl hydrazone sodium salt: Isolated as a white solid, $u_{max}$ (KBr disc)/cm$^{-1}$ 3518, 1236, 1137,1090, 1044, 662; $d_H$ ($D_2O$) 2.23 (3H,s), 2.26 (3H,s), 7.11 (2H,d, J 8), 7.26 (2H,d, J 8), 7.37 (2H,d, J 8), 7.70 (2H,d, J 8), 7.89 (1H,s); $d_C$ ($D_2O$) 20.3 (q), 20.5 (q), 126.4 (d), 126.5 (d), 129.2 (d), 129.3 (d), 132.7 (s), 139.2 (s), 142.5 (s), 146.0 (d); m/z (FAB) 311 (M$^+$+1, 41%), 308 (25), 307 (100); (Found [M+H]$^+$ 311.0834. $C_{15}H_{16}N_2O_2SNa$ requires m/z, 311.0830).

4-Chlorobenzaldehyde tosyl hydrazone sodium salt: Isolated as an off-white solid, $u_{max}$ (KBr disc)/cm$^{-1}$ 1239, 1129, 1087, 1062, 1030; $d_H$ ($D_2O$) 2.10 (3H,s), 7.05–7.12 (4H,m), 7.28 (2H,d, J 8), 7.65 (2H,d, J 8), 7.80 (1H,s); $d_C$ ($D_2O$) 20.4 (q), 126.5 (d), 127.5 (d), 128.3 (d), 129.3 (d), 133.3 (s), 134.2 (s), 139.1 (s), 142.2 (s), 144.2 (d); m/z (FAB) 331 (M$^+$+1, 80%); (Found [M+H]$^+$ 331.0278. $C_{14}H_{12}N_2O_2SClNa$ requires m/z, 331.0284).

3-Nitrobenzaldehyde tosyl hydrazone sodium salt: Isolated as a yellow solid, (Found C, 49.14; H, 3.50; N, 12.0. $C_{14}H_{12}N_3O_4SNa$ requires C, 49.3; H, 3.5; N, 12.3%); $u_{max}$ (KBr disc)/cm$^{-1}$ 1530, 1351, 1237, 1142, 1127, 1084, 1041; $d_H$ ($D_2O$) 2.14 (3H,s), 7.13–7.21 (3H,m), 7.55 (1H,d, J 7.5), 7.58–7.76 (3H,m), 7.77 (1H,s), 8.01 (1H,m; $d_C$ ($D_2O$) 20.4 (q), 120.1 (d), 122.2 (d), 126.6 (d), 129.2 (d), 132.2 (d), 137.3 (s), 139.0 (s), 142.0 (d), 142.4 (s), 147.5 (s); m/z (FAB) 342 (M$^+$+1, 22%), 201 (56).

4-Methoxybenzaldehyde tosyl hydrazone sodium salt: Isolated as a white solid, $u_{max}$ (KBr disc)/cm$^{-1}$ 1511, 1248, 1234, 1141, 1088, 1031; $d_H$ ($D_2O$) 2.20 (3H,s), 3.66 (3H,s), 6.77 (2H,d, J 8), 7.20 (2H,d, J 8), 7.37 (2H,d, J 8), 7.68 (2H,d, J 8.2), 7.86 (1H,s); $d_C$ ($D_2O$) 20.4 (q), 55.2 (q), 113.9 (d), 126.5 (d), 127.8 (d), 128.7 (s), 129.3 (d), 139.3 (s), 142.4 (s), 145.6 (d), 159.1 (s); m/z (FAB) 327 (M$^+$+1, 100%), 298 (40); (Found [M+H]$^+$ 327.0779. $C_{15}H_{16}N_2O_3SNa$ requires m/z, 327.0799).

4-Cyanobenzaldehyde tosyl hydrazone sodium salt: Isolated as a pale yellow solid, $u_{max}$ (KBr disc)/cm$^{-1}$ 3064, 2225, 1238, 1133, 1087, 1045; $d_H$ ($D_2O$) 2.16 (3H,s), 7.18 (2H,d, J 8), 7.40 (4H,m), 7.67 (2H,d, J 8), 7.81 (1H,s); $d_C$ ($D_2O$) 20.5 (q), 119.5 (s), 126.4 (d), 126.5 (d), 129.4 (d), 132.5 (d), 140.9 (s), 143.3 (d), 143.5 (s) (2 ipso C's not observed); m/z (FAB) 322 (M$^+$+1, 12%), 201 (100).

2,4,6-Trimethylbenzaldehyde tosyl hydrazone sodium salt: This compound appeared to decompose slowly at room temperature and was therefore stored at +4° C. Isolated as a white solid, $u_{max}$ (KBr disc)/cm$^{-1}$ 2965, 1247, 1232,1136, 1091; $d_H$ ($D_2O$) 2.01 (6H,s), 2.14 (3H,s), 2.31 (3H,s), 6.75 (2H,s), 7.26 (2H,d, J 8), 7.68 (2H,d, J 8), 8.05 (1H,s); $d_C$ ($D_2O$) 19.5 (q), 20.0 (q), 20.5 (q), 126.9 (d), 128.4 (d), 129.3 (d), 130.5 (s), 137.2 (s) 138.1 (s), 139.3 (s), 142.5 (s), 145.4 (d); m/z (FAB) 339 (M$^+$+1, 100%); (Found [M+H]$^+$ 339.1146. $C_{17}H_{20}N_2O_2SNa$ requires m/z, 339.1143).

Pivaldehyde tosyl hydrazone sodium salt: Isolated as a white solid, $u_{max}$ (KBr disc)/cm$^{-1}$ 2960, 1244, 1136, 1095; $d_H$ ($D_2O$) 0.97 (9H,s), 2.41 (3H,s), 7.22 (1H,s), 7.30 (2H,d, J 8), 7.64 (2H,d, J 8); $d_C$ ($D_2O$) 20.4 (q), 26.9 (q), 33.6 (s), 126.4 (d), 129.2 (d), 140.5 (s), 142.3 (s), 159.1 (d); m/z (FAB) 277 (M$^+$+1,73%); (Found [M+H]$^+$ 277.0982. $C_{12}H_{18}N_2O_2SNa$ requires m/z, 277.0987).

Acetophenone tosyl hydrazone sodium salt: Isolated as a white solid, $d_H$ ($D_2O$) 2.19 (3H,s), 2.25 (3H,s), 7.19–7.34 (5H,m), 7.45–7.55 (2H,m), 7.74 (2H,d, J 8).

Benzaldehyde tosyl hydrazone lithium salt: This compound was prepared according to the above method using benzaldehyde tosyl hydrazone (3.65 mmol) and lithium methoxide (prepared in situ from lithium and anhydrous methanol). The salt was isolated as an off-white solid which appeared less stable at room temperature than the corresponding sodium derivative. It was, however, stable for long periods of time if stored at +4° C., $u_{max}$ (KBr disc)/cm$^{-1}$ 3060, 1238, 1132, 1088, 1034; $d_H$ (D$_2$O) 2.24 (3H,s), 7.19–7.35 (5H,m), 7.41–7.54 (2H,m), 7.70 (2H,d, J 8.5), 7.93 (1H,s); m/z (FAB) 281 (M$^+$+1, 35%), 160 (100).

Benzaldehyde tosyl hydrazone tetrabutylammonium salt: This compound was prepared according to the above method using benzaldehyde tosyl hydrazone (10.9 mmol) and a commercially available 1M solution of tetrabutylammonium hydroxide in methanol. The salt was isolated as an off-white solid. The compound appeared somewhat unstable at room temperature and was thus stored at −20° C., $u_{max}$ (KBr disc)/cm$^{-1}$ 2961, 1248, 1129, 1073, 1044; $d_H$ 0.89 (12H,t, J 7.5), 1.25–1.57 (16H,m), 2.28 (3H,s), 3.10–3.19 (8H,m), 6.95–7.35 (6H,m), 7.46 (2H,d, J 8.8), 7.82 (2H,d, J 8.8); $d_C$ (D$_2$O) 13.7 (q), 19.7 (t), 21.3 (q), 24.0 (t), 58.5 (t), 124.7 (d), 125.5 (d), 127.0 (d), 127.9 (d), 128.4 (d), 138.6 (s), 138.8 (s), 138.9 (d), 143.6 (s); m/z (FAB) 758 ([M+H]$^+$+NBu$_4$,100%), 516 (M$^+$+1, 15%).

General Epoxidation Procedure Using Benzaldehyde Tosyl Hydrazone Sodium Salt and Achiral Sulphides To a rapidly stirred solution of tetrahydrothiophene (20 mol %, 5.8 mg, 0.066 mmol), rhodium (II) acetate dimer (1 mol %, 1.5 mg, 0.003 mmol), benzyltriethylammonium chloride (20 mol %, 15 mg, 0.066 mmol) and an aldehyde (0.33 mmol) in anhydrous acetonitrile (1 cm$^3$) was added the tosyl hydrazone salt (1.5 equivalents, 147 mg, 0.495 mmol). The heterogeneous mixture was stirred rapidly at room temperature to facilitate even dispersion of the solid, then heated at 45° C. (bath temperature) for 3–5 hours (or until TLC showed that all of the aldehyde had been consumed). The mixture was then cooled and ethyl acetate/water (0.5 cm$^3$+0.5 cm$^3$) added. The organic phase was removed and the aqueous phase extracted with ethyl acetate (2×0.5 cm$^3$). The combined organic extracts were then dried over sodium sulphate, filtered and concentrated in vacuo. The residue was purified on silica, eluting with 0–25% DCM/petrol, to give the desired epoxide.

Stilbene oxide: Isolated as a white solid (62 mg, 95%) and as a >98:2 mixture of trans:cis diastereoisomers, R$_f$=0.70 (10% EtOAc/petrol); $d_H$ trans isomer 3.85 (2H,s), 7.16–7.37 (10H,m); cis isomer 4.28 (2H,s), 7.01–7.15 (10H,m).

2-(4-Chlorobenzenyl)-3-phenyl oxirane: Isolated as a white solid (66 mg, 86%) and as a >98:2 (trans:cis) mixture of diastereoisomers, R$_f$=0.65 (10% EtOAc/petrol); $d_H$ trans isomer 3.82 (1H,d, J 1.8), 3.85 (1H,d, J 1.8), 7.04–7.50 (9H,m); cis isomer 4.31 (1H,d, J 4.6), 4.37 (1H,d, J 4.6), 7.04–7.50 (9H,m).

2-(4-Methylbenzenyl)-3-phenyl oxirane: Isolated as a colourless oil (67 mg, 97%) and as a >98:2 (trans:cis) mixture of diastereoisomers, R$_f$=0.70 (10% EtOAc/petrol); $d_H$ trans isomer 2.37 (3H,s), 3.83 (1H,d, J 1.5), 3.86 (1H,d, J 1.5), 7.16–7.44 (9H,m); cis isomer. 2.15 (3H,s), 4.24 (2H,m), 6.89–7.40 (9H,m).

2-(4-Nitrobenzenyl)-3-phenyl oxirane: This compound was purified on silica, eluting with 0–20% EtOAc/petrol. Isolated as a white solid (75 mg, 94%) and as a single (trans) diastereoisomer, R$_f$=0.68 (30% EtOAc/petrol); $d_H$ 3.85 (1H, d, J 1.9), 3.98 (1H,d, J 1.9), 7.30 (7H,m), 8.30 (2H,m).

2-(4-Methoxybenzenyl)-3-phenyl oxirane: This compound was purified on silica, eluting rapidly with 0–20% EtOAc/petrol. Isolated as a colourless oil (73 mg, 98%) and as a >98:2 (trans:cis) mixture of diastereoisomers, R$_f$=0.50 (10% EtOAc/petrol); $d_H$ trans isomer 3.71 (3H,s), 3.73 (1H,d, J 1.8), 3.78 (1H,d, J 1.8), 6.93–7.41 (9H,m); cis isomer. 3.61 (3H,s), 4.23 (1H,d, J 1.6), 4.24 (1H,d, J 1.6), 6.81–7.40 (9H,m).

2-n-Butyl-3-phenyl oxirane: Isolated as a colourless oil (34 mg, 59%) and as a 70:30 mixture (trans:cis) of diastereoisomers, R$_f$=0.30 (10% EtOAc/petrol); $d_H$ trans isomer 0.75–1.01 (3H,m), 1.11–1.74 (6H,m), 2.86 (1H,dt, J 5.5 and 2.1), 3.52 (1H,d, J 2.1), 7.01–7.35 (5H,m); cis isomer 0.75–1.01 (3H,m), 1.11–1.74 (6H,m), 3.17 (1H,m), 4.05 (1H,d, J 4.2), 7.01–7.35 (5H,m).

2-Cyclohexyl-3-phenyl oxirane: Isolated as a colourless oil (46 mg, 69%) and as a 65:35 mixture (trans:cis) of diastereoisomers, R$_f$=0.41 (10% EtOAc/petrol); $d_H$ trans isomer 0.76–2.09 (11H,m), 2.76 (1H,dd, J 6.8 and 2.1), 3.68 (1H,d, J 2.1), 7.15–7.23 (5H,m); cis isomer 0.76–2.09 (11H, m), 2.86 (1H,dd, J 8.9 and 4.2), 4.05 (1H, J 4.2), 7.15–7.23 (5H,m).

2-(trans-2-Phenylethylene)-3-phenyl oxirane: This compound was purified on silica, eluting rapidly with 0–20% EtOAc/petrol. Isolated as a colourless oil (71 mg, 97%) and as a single (trans) diastereoisomer, R$_f$=0.42 (10% EtOAc/petrol); $d_H$ 3.52 (1H,dd, J 8 and 2), 3.88 (1H,dd, J 2), 6.06 (1H,dd, J 16 and 8), 6.72 (1H,d, J 16), 7.15–7.50 (10H,m).

3-(3-Phenyl-oxirane)-pyridine: This compound was purified on silica, eluting with 0–50% EtOAc/petrol. Isolated as a colourless oil (46 mg, 71%) and as a single, trans, diastereoisomer, R$_f$=0.37 (50% EtOAc, petrol); $d_H$ 3.87 (2H,m), 7.12–7.50 (6H,m), 7.55–7.75 (1H,m), 8.59 (2H,m); $d_C$ 60.7 (d), 62.8 (d), 123.5 (d), 125.5 (d), 128.7 (d), 132.7 (d), 136.4 (s), 140.0 (s), 147.8 (d), 149.7 (d).

2-t-Butyl-3-phenyl oxirane: This compound was prepared according to the above general method using pivaldehyde tosyl hydrazone sodium salt (0.495 mmol, 137 mg). The epoxide was isolated as a colourless oil (4 mg, 6%) and as a single (trans) diastereoisomer, R$_f$=0.64 (10% EtOAc/petrol); $d_H$ 0.94 (9H,s), 2.69 (1H,m), 3.66 (1H,m), 7.01–7.35 (5H,m).

2,3-Diphenyl-2-methyl oxirane: This compound was prepared according to the above general method using acetophenone tosyl hydrazone sodium salt (0.495 mmol, 153 mg) and copper (II) acetylacetonate (5 mol %, 5 mg). The reaction was carried out at 55° C. The epoxide was isolated as a white solid (16 mg, 18%) and as a single diastereoisomer, R$_f$=0.45 (10% EtOAc/petrol); $d_H$ 1.80 (3H, s), 4.23 (1H,s), 7.05–7.55 (10H,m).

Epoxidation Using Ketones as Substrates

The reactions were carried out according to the above general method using pentamethylene sulphide (20 mol %, 0.066 mmol, 7 mg).

2-(4-Nitrobenzenyl)-2-methyl-3-phenyl oxirane: Isolated as a pale yellow solid (72 mg, 69%) and as a single (trans) diastereoisomer, R$_f$=0.58 (20% EtOAc/petrol); $d_H$ 1.78 (3H, s), 4.25 (1H,s), 6.95–7.45 (7H,m), 8.05 (2H,m).

Epoxide derived from cyclohexanone: Isolated as a colourless oil; the product was impure and the yield was estimated by NMR analysis as 54% . Only the trans isomer was observed; R$_f$=0.78 (10% EtOAc/petrol); $d_H$ 1.15–2.05 (10H,m), 3.82 (1H,s), 7.15–7.40 (5H, m).

2,3-Diphenyl-2-methyl oxirane: Isolated as a colourless oil; the product was impure and the yield was estimated by NMR analysis as 15%. Only the trans isomer was observed. The data for this compound is reported above.

Epoxidation Using Substituted Aryl Tosyl Hydrazone Sodium Salts

The reactions were carried out according to the above general procedure using the appropriate substituted aryl tosyl hydrazone sodium salts (prepared as described above, 0.495 mmol) and benzaldehyde (0.33 mmol).

2-(4-Chlorobenzenyl)-3-phenyl oxirane: Isolated as a white solid (72 mg, 95%) and as a >98:2 (trans:cis) mixture of diastereoisomers. The NMR data for this compound is reported above.

2-(4-Methylbenzenyl)-3-phenyl oxirane: Isolated as a colourless oil (50 mg, 73%) and as a 80:20 mixture (trans:cis) of diastereoisomers. The NMR data for this compound is reported above.

2-(4-Methoxybenzenyl)-3-phenyl oxirane: This compound was purified on silica, eluting rapidly with 0–20% EtOAc/petrol. Isolated as a colourless oil (71 mg, 96%) and as a 67:33 mixture (trans:cis) of diastereoisomers. The NMR data for this compound is reported above.

2-(4-Cyanobenzenyl)-3-phenyl oxirane: Isolated as a colourless oil (65 mg, 89%) and as a single (trans) diastereoisomer, $R_f$=0.69 (10% EtOAc/petrol); $d_H$ 3.75 (1H, d, J 1.75), 3.85 (1H,d, J 1.75), 7.10–7.71 (9H,m).

2-(2,4,6-Trimethylbenzenyl)-3-phenyl oxirane: Isolated as a colourless oil (13 mg, 17%) and as a single (trans) diastereoisomers, $R_f$=0.53 (15% EtOAc/petrol), m.p. 66–68° C.; (Found C, 85.45; H, 7.58. $C_{17}H_{18}O$ requires C, 85.6; H, 7.6%); $u_{max}$ (KBr disc)/cm$^{-1}$ 2971, 2918, 1607, 890, 792; $d_H$ 2.28 (3H,s), 2.41 (6H,s), 3.82 (1H,d, J 2.1), 3.90 (1H,m), 6.86 (2H,s), 7.29–7.54 (5H,m); $d_C$ 19.9 (q), 21.0 (q), 60.0 (d), 62.1 (d), 125.5 (d), 128.3 (d), 128.6 (d) 128.7 (d), 131.0 (s), 137.1 (s), 137.5 (s); m/z (EI) 238 (M$^+$, 26%), 132 (100), 117 (97), 223 (48).

2-(3-Nitrobenzenyl)-3-phenyl oxirane: Isolated as an oil (contaminated with unreacted benzaldehyde). Yield estimated by NMR analysis 74%. Only the trans isomer was observed. $R_f$=0.52 (10% EtOAc/petrol); $d_H$ 3.81 (1H,d, J 1.9), 3.94 (1H,d, J 1.9), 7.10–7.68 (7H,m), 8.12 (2H,m).

Epoxidation Using Benzaldehyde Tosyl Hydrazone Lithium Salt

The reaction was carried out according to the above general procedure using benzaldehyde tosyl hydrazone lithium salt (prepared as described above, 2.5 equivalents, 0.825 mmol, 231 mg), copper (II) acetylacetonate (5 mol %, 5 mg) and 4-chlorobenzaldehyde (47 mg, 0.33 mmol). The reaction mixture was homogeneous during the experiment. The epoxide was isolated as a white solid (41 mg, 54%) and as a 2.8:1 (trans:cis) mixture of diastereoisomers. The NMR data for this compound is reported above.

Epoxidation Using Benzaldehyde Tosyl Hydrazone Tetrabutylammonium Salt

The reaction was carried out according to the above general procedure using benzaldehyde tosyl hydrazone tetrabutylammonium salt (prepared as described above, 255 mg), copper (II) acetylacetonate (5 mol %, 5 mg) and 4-chlorobenzaldehyde (47 mg, 0.33 mmol). The reaction mixture was homogeneous during the experiment. The epoxide was isolated as a white solid (45 mg, 60%) and as a >98:2 (trans:cis) mixture of diastereoisomers. The NMR data for this compound is reported above.

Epoxidation Using Aqueous Acetonitrile as Solvent System

The reaction was carried out according to the above general procedure using copper (II) acetylacetonate (5 mol %, 5 mg) and 4-chlorobenzaldehyde (47 mg, 0.33 mmol) in water/acetonitrile (0.5 cm$^3$+0.5 cm$^3$). The reaction mixture was homogeneous in this solvent system.

Benzaldehyde tosyl hydazone sodium salt (3 equivalents, 1 mmol, 296 mg) gave the epoxide as a white solid (68 mg, 89%) and as a 2.6:1 mixture (trans:cis) of diastereoisomers.

Benzaldehyde tosyl hydrazone lithium salt (2.5 equivalents, 0.825 mmol, 231 mg) gave the epoxide as a white solid (66 mg, 86%) and as a 2.8:1 mixture (trans:cis) of diastereoisomers. The NMR data for the epoxide is reported above.

Preparation of a Sulphide of Formula (D) Wherein $R^a$ is $CH_2OCH_3$ and $R^b$ is H (10)-Mercaptoisoborneol and (10)-mercaptoborneol were prepared by modifying the procedure of Eliel (J. Org. Chem. 1979, 44, 3598).

A solution of (+)-(10)-camphorsulphonyl chloride (commercial material, purified by recrystallisation from DCM/hexane) (2.56 g, 10.21 mmol) in anhydrous diethyl ether (50 cm$^3$) was added dropwise to a stirred suspension of lithium aluminium hydride (1.94 g, 51.11 mmol) in anhydrous diethyl ether (50 cm$^3$) at 0° C. over 1 hour. Once the addition was complete, stirring was continued for a further 2 hours at 0° C. The mixture was then allowed to warm to room temperature and refluxed for a further 4 hours. The reaction mixture was then allowed to cool to room temperature. Excess hydride was quenched by the cautious addition of iced water followed by dilute HCl (aq.) (20 cm$^3$). Rochelle's salt was then added (5.0 g) and stirring continued for 5 minutes before filtration through CELITE™. The aluminium residues were then washed with copious quantities of diethyl ether. The filtrate was washed with water (3×50 cm$^3$) and brine (3×50 cm$^3$) then dried over magnesium sulfate. Removal of the solvent in vacuo gave the crude product which was purified on silica, eluting with 98:2 petrol/EtOAc. (10)-Mercaptoisoborneol was obtained as a waxy solid (1.13 g, 59%), [a]$^{20}_D$–56.2 (c 5.1, CHCl$_3$); $d_H$ 0.83 (3H,s), 1.05 (3H,s), 1.28 (1H,dd, J 6 and 10), 0.95–1.80 (7H,m), 1.95 (1H,brs), 2.56 (1H,dd, J 12 and 6), 2.79 (1H,dd, J 12 and 10), 3.97–4.04 (1H,m). (10)-mercaptoborneol was eluted second as a white solid (250 mg, 13%), [a]$^{20}_D$–13.1 (c 9, CHCl$_3$); (Found: C, 64.44; H, 9.66; S, 17.16. $C_{10}H_{18}OS$ requires C, 64.5; H, 9.7; S, 17.2%); $d_H$ 0.80–2.36 (9H,m), 0.90 (6H,s), 2.52 (1H,dd, J 10 and 10), 2.73 (1H,dd, J 10 and 7), 4.31–4.39 (9H,m).

To a cooled solution (0° C.) of (+)-(10)-mercaptoisoborneol (0.52 g, 2.80 mmol) and methoxyacetaldehyde dimethyl acetal (1.05 cm$^3$, 8.39 mmol) in dichloromethane (6 cm$^3$) under nitrogen or argon, was added boron trifluoride etherate (0.39 cm$^3$, 3.08 mmol). After a few minutes the reaction mixture was loaded directly onto a silica gel column and eluted with 50% DCM/petrol to give the oxathiane as a pale yellow oil (637 mg, 94%), $R_f$=0.83 (20% EtOAc/petrol); [a]$^{20}_D$–126.1 (c 1.11, CHCl$_3$); $u_{max}$ (film)/cm$^{-1}$ 2940, 2872, 1121, 1067; $d_H$ 0.78–2.00 (13H,m), 2.75 (1H,d, J 14), 3.09 (1H, , J 14), 3.38 (3H,s), 3.46 (1H,dd, J 10.5 and 4), 3.58 (2H,m), 4.90 (1H,dd, J 7 and 4); $d_C$ 20.4 (q), 23.2 (q), 27.3 (t), 28.3 (t), 34.4 (t), 37.9 (t), 42.5 (s), 45.5 (d), 46.7 (s), 59.4 (q), 74.8 (t), 80.7 (d), 85.2 (d), m/z (EI) 242 (M$^+$, 13%), 197 (100), 135 (70), 93 (27); (Found [M]$^+$ 242.1344. $C_{13}H_{22}O_2S$ requires m/z, 242.1341).

General Procedure for Epoxidation Using Benzaldehyde Tosyl Hydrazone Sodium Salt and a Sulphide of Formula (D) Wherein $R^a$ is $CH_2OCH_3$ and $R^b$ is H To a rapidly stirred solution of a sulphide of formula (D) wherein $R^a$ is $CH_2OCH_3$ and $R^b$ is H (1 equivalent, 80 mg, 0.33 mmol), rhodium (II) acetate dimer (1 mol %, 1.5 mg, 0.003 mmol), benzyltriethylammonium chloride (20 mol %, 15 mg, 0.066 mmol) and benzaldehyde (35 mg, 0.33 mmol) in anhydrous acetonitrile (1 cm$^3$) was added the tosyl hydrazone salt (1.5 equivalents, 147 mg, 0.495 mmol). The heterogeneous mixture was stirred rapidly at room temperature to facilitate even dispersion of the solid, then held at 30° C. (bath temperature) for 32 hours. The mixture was then cooled and ethyl acetate/water (0.5 cm$^3$+0.5 cm$^3$) added. The organic phase was removed and the aqueous phase extracted with ethyl acetate (2×0.5 cm$^3$). The combined organic extracts were then dried over sodium sulphate, filtered and concentrated in vacuo. The residue was purified on silica, eluting with 0–25% DCM/petrol, to give stilbene oxide as a white solid (38 mg, 59%) and as a >98:2 mixture (trans:cis) of diastereoisomers; enantiomeric excess 93% (R, R major) as determined by chiral HPLC (see conditions below). The NMR data for this compound is reported above.

Determination of Enantiomeric Excess

Column 25 cm, 4.6 mm internal diameter, stainless steel column packed with chiracell OD stationary phase.
Mobile phase 1% iso-propyl alcohol/99% petroleum ether (40–65° C.).
Flow rate 2 cm$^3$ min$^{-1}$
Temperature Ambient
Detection 254–240 nm
Standard A racemic sample was run to check the retention times of the enantiomers. The chromatogram was recorded using a diode array detector to confirm the physical relationship between the enantiomers.
Retention Major enantiomer (R, R) 5.99 minutes. [Absolute configuration
times determined by comparison of [a]$_D$ with literature values (see J. Org. Chem. 1979, 44, 2505).] Minor enantiomer (S, S) 4.52 minutes.

Following the above process and using the same substrates, except that different sulphides of formula (D) were used, gave the following results.

| R$^a$ | R$^b$ | Isolated yield epoxide | selectivity trans:cis | ee | Comments |
|---|---|---|---|---|---|
| CH$_3$ | H | <5% | >98:2 | 90% | |
| CH$_2$OCH$_3$ | H | 56% | >98:2 | 94% | Room temperature, 3 days |
| CH$_2$O(CH$_2$)$_3$CH$_3$ | H | 27% | >98:2 | | |
| OCOCH$_3$ | H | 22% | >98:2 | | |

Cyclopropanation of Chalcone Using Benzaldehyde Tosyl Hydrazone Sodium Salt

To a rapidly stirred solution of pentamethylene sulphide (1 equivalent, 0.10 cm$^3$,1 mmol), rhodium (II) acetate dimer (1 mol %, 4 mg, 0.01 mmol), benzyltriethylammonium chloride (20 mol %, 45.5 mg, 0.2 mmol) and trans chalcone (208 mg, 1 mmol) in anhydrous acetonitrile (3 cm$^3$) was added the tosyl hydrazone salt (1.5 equivalents, 440 mg, 1.5 mmol). The heterogeneous mixture was stirred rapidly at room temperature to facilitate even dispersion of the solid, then heated at 45° C. (bath temperature) for 22 hours. The mixture was then cooled and ethyl acetate/water (5 cm$^3$+5 cm$^3$) added. The organic phase was removed and the aqueous phase extracted with ethyl acetate (2×5 cm$^3$). The combined organic extracts were then dried over sodium sulphate, filtered and concentrated in vacuo. The residue was purified on silica, eluting with 0–50% DCM/petrol, to give the cyclopropane as a white solid (131 mg, 44%) and as a 70:30 mixture (trans:cis) of diastereoisomers, m.p. (mixture) 144–146° C.; d$_H$ trans isomer: 3.28 (1H,dd, J 7 and 5.5), 3.38 (1H,dd, J 9.5 and 7), 3.65 (1H dd, J 9.5 and 5.5), 7.01–7.65 (13H,m), 7.95 (2H,m); cis isomer: 3.33 (2H,d, J 5.5), 3.55 (1H,t, J 5.5), 7.01–7.65 (13H,m) 8.20 (2H,m).

Aziridination of N-Benzylidenetoluene-p-sulphonamide Using Benzaldehyde Tosyl Hydrazone Sodium Salt To a rapidly stirred solution of tetrahydrothiophene (1 equivalent, 0.34 mmol, 0.03 cm$^3$), rhodium (II) acetate dimer (1 mol %, 1.5 mg, 0.003 mmol), benzyltriethylammonium chloride (20 mol %, 15 mg, 0.066 mmol) and imine (89 mg, 0.33 mmol) in anhydrous acetonitrile (1 cm$^3$) was added the tosyl hydrazone salt (1.5 equivalents, 147 mg, 0.495 mmol). The heterogeneous mixture was stirred rapidly at room temperature to facilitate even dispersion of the solid, then heated at 45° C. (bath temperature) for 3 hours . The mixture was then cooled and ethyl acetate/water (0.5 cm$^3$+ 0.5 cm$^3$) added. The organic phase was removed and the aqueous phase extracted with ethyl acetate (2×0.5 cm$^3$). The combined organic extracts were then dried over sodium sulphate, filtered and concentrated in vacuo. The residue was purified on silica, eluting with 0–25% EtOAc/petrol, to give the aziridine as a white solid (63 mg, 96%) and as a 3:1 (trans:cis) mixture of diastereoisomers, cis isomer R$_f$0.32 (10% EtOAc/petrol); m.p. 153–154° C.; d$_H$ 2.42 (3H,s), 4.21 (2H,s), 7.00–7.10 (10H,m), 7.34 (2H,d, J 8), 7.98 (2H,d, J 8); trans isomer R$_f$0.30 (10% EtOAc/petrol); m.p. 138° C.; d$_H$ 2.38(3H,s), 4.24(2H,s), 7.22(2H,d, J 8), 7.30–7.44(10H, m), 7.60(2H,d, J 8).

In Situ Epoxidation Using a Sulphide of Formula (J) Wherein R' is Hydrogen

Cuprous bromide (7 mg, 0.05 mm, 10 mol %) was placed in a vial under argon and a sulphide of formula (J) wherein R' is hydrogen (11 mg, 0.05 mmol, 10 mol %) in DCM (1 cm$^3$) added. A green solution formed which was stirred at room temperature for 2 hours before the solvent was removed by a steady stream of argon. The residue was dissolved in acetonitrile (1.5 cm$^3$) and 4-chlorobenzaldehyde (70 mg, 0.5 mmol) added. Benzyltriethylammonium chloride (23 mg, 0.1 mmol, 20 mol %) was added followed by benzaldehyde tosyl hydrazone sodium salt (0.75 mmol, 222 mg). The rapidly stirring mixture was heated to 40° C. overnight. The epoxide produced was purified by column chromatography (10% DCM/petrol) and furnished as a white solid (56 mg, 49%) and as a single (trans) diastereoisomer. The NMR data for this compound is reported above.

Preparation of (1S, 4R)-10-Mercaptomethyl-7,7-dimethyl-bicyclo [2.2.1]heptan-2-one 1

(+)-(10)-Camphorsulfonyl chloride (12.0 g, 48 mmol), and triphenylphosphine (50.1 g, 191 mmol) were refluxed in a mixture of water (40 mL) and 1,4-dioxane (160 mL) for one hour under nitrogen. After the reaction mixture had cooled it was extracted with petrol (200 mL and 3×100 mL). The combined organic extracts were washed with water (2×100 mL) and brine (100 mL) before drying over MgSO$_4$. After filtration and removal of the solvents under reduced pressure, the resulting oil was loaded directly onto a silica gel column and eluted with 5% ethyl acetate in petrol to give thiol 1 as a white crystalline solid (7.3 g, 82%), m.p. 62–65° C. [Lit., 65–66° C.]; $d_H$ (250 MHz; CDCl$_3$) 0.89 (3H, s, CH$_3$), 1.00 (3H, s, CH$_3$), 1.21–2.01 (6H, m), 2.07 (1H, t, J 4.6), 2.26–2.43 (2H, CHHS, (CO)CHH), 2.85 (1H, dd, J 13.7, 6.7, CHHS), [lit., $d_H$ (CCl$_4$) 0.93 (3H, s), 1.05 (3H, s), 1.2–2.6 (8H, m), 2.73 (1H, d, J 6), 2.95 (1H, d, J 6)]; $d_C$ (63 MHz; CDCl$_3$) 19.83 (CH$_3$), 20.31 (CH$_3$), 21.40 (CH$_2$), 26.63 (CH$_2$), 27.06 (CH$_2$), 29.92 (C), 43.29 (CH$_2$), 43.67 (CH), 47.85 (C), 60.65 (C).

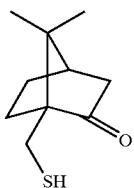

1

Preparation of (1S, 2S, 4R)-1-Mercaptomethyl-7.7-dimethyl-2-(trimethyl-silanylethynyl)-bicyclo[2.2.1]heptan-2-ol 2

Trimethylsilylacetylene (0.15 mL, 1.1 mmol) was added dropwise to a −78° C. solution of butyllithium (0.32 mL of a 2.5M solution in hexanes) in tetrahydrofuran (0.5 mL) under nitrogen. After thirty minutes a solution of 1 (50 mg, 0.27 mmol) in tetrahydrofuran (0.5 mL) was added to the reaction mixture and the resulting solution stirred for three hours at −78° C. The reaction mixture was warmed to room temperature before being quenched with saturated ammonium chloride solution. The organic phase was separated and the aqueous phase extracted with ethyl acetetate before drying the combined organic phases over MgSO$_4$. After filtration and removal of the solvents, the desired alcohol 2 was obtained (65 mg, 84%), $[a]^{20}_D$+9.3 (c 2.68 in CHCl$_3$); $u_{max}$ (thin film)/cm$^{-1}$ 3462 (OH), 2956 (CH), 2161 (SH), 842 (TMS); $d_H$ (250 MHz; CDCl$_3$) 0.08–0.21 (9H, m SiCH$_3$), 0.90 (3H, s, CH$_3$), 1.60 (3H, s, CH$_3$), 0.77–1.29 (3H, m), 1.49–183 (4H,m), 2.12–2.42 (2H, m), 2.53 (1H, dd, J 13.0, 7.5, CHHS), 3.01 (1H, dd, J 13.0, 7.0, CHHS); $d_C$ (63 MHz; CDCl$_3$) −0.24 (CH$_3$), 20.82 (CH$_3$), 21.63 (CH$_3$), 23.40 (CH$_2$), 26.51 (CH$_2$), 29.35 (CH$_2$), 45.84 (CH), 49.53 (C), 49.72 (CH$_2$), 56.30 (C), 89.91 (C), 11.27 (C), quaternary not visible; m/z (EI) 282 (M$^+$, 46%), 233 (27), 108 (52), 73 (100), (Found; M$^+$, 282.1472. C$_{15}$H$_{26}$OSSi requires 282.1474).

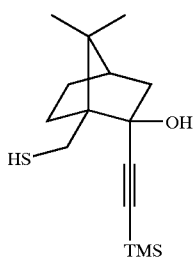

2

Preparation of (1S, 5R, 7R)-10,10-Dimethyl4-methylene-3-thia-tricyclo[5.2.1.0$^{1,5}$]decan-5-ol 3

Tetrabutylammonium fluoride (0.5 mL of a 1.0M solution in tetrahydrofuran) was added to a solution of alcohol 2 (65 mg, 0.23 mmol) in tetrahydrofuran (5 mL) under nitrogen. After two hours water was added to the solution and the resulting mixture extracted with dichloromethane. The combined organic extracts were washed with brine and dried over MgSO$_4$. After filtration and removal of the solvents under reduced pressure, chromatography with 5% ethyl acetate in petrol gave sulfide 3 (31 mg, 64%), $[a]^{20}_D$−90.5 (c 2.10 in CHCl$_3$); $u_{max}$ (thin film)/cm$^{-1}$ 3483 (OH), 2942 (CH), 1701 (C=C), 1627 (C=C); $d_H$ (250 MHz; CDCl$_3$) 0.97 (3H, s, CH$_3$), 1.01–1.16 (1H, m), 1.27 (3H, s, CH$_3$), 1.50–1.83 (4H, m), 1.96–2.10 (2H, m), 2.14 (1H, br s, OH), 2.52 (1H, d, J 9.0, CHHS), 3.22 (1H, d, J 9.0, CHHS), 4.93 (1H, d, J 1.0, =CHH), 5.12 (1H, d, J 1.0, =CHH); $d_C$ (63 MHz; CDCl$_3$) 22.02 (CH$_3$), 22.05 (CH$_3$), 26.89 (CH$_2$), 31.95 (CH$_2$), 32.07 (CH$_2$), 37.38 (CH$_2$), 46.25 (C), 50.79 (CH), 61.68 (C), 93.20 (C), 101.39 (CH$_2$), 151.81 (C); m/z (EI) 210 (M$^+$, 30%), 108 (57), 95 (100), 81 (27), (Found; M$^+$, 210.1085. C$_{12}$H$_{18}$OS requires 210.1078).

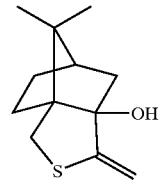

3

Preparation of (1S, 5R, 7R)-10,10-Dimethyl-4-methylene-3-thia-5-trimethylsilyloxy-tricyclo[5.2.1.0$^{1,5}$]decan 4

A mixture of N-trimethylsilylimidazole (1.71 mL, 11.6 mmol) and alcohol 3 (95 mg, 0.45 mmol) were heated at 100° C. for 90 minutes under nitrogen. After cooling at room temperature the mixture was diluted with petroleum ether, washed with water and dried over MgSO$_4$. After filtration and removal of the solvents under reduced pressure, chromatography with petrol gave sulfide 4 (120 mg, 94%), $u_{max}$ (thin film)/cm$^{-1}$ 2941 (CH), 1622 (C=C), 1247 (SiCH$_3$), 1082 (SiO); $d_H$ (250 MHz; CDCl$_3$) 0.10 (s, 9H), 0.94 (s, 3H), 1.22 (s, 3H), 0.80–1.10 (m, 1H), 1.20–2.05 (m, 6H), 2.36–2.39 (d, J8.5, 1H), 3.24–3.27 (d, J8.3, 1H), 4.93 (s, 1H), 5.07 (s, 1H); $d_C$ (63 MHz; CDCl$_3$) 1.7 (CH$_3$), 22.2 (CH$_3$), 22.6 (CH$_3$), 26.7 (CH$_2$), 31.1 (CH$_2$), 32.3 (CH$_2$), 39.1 (CH$_2$), 46.1 (C), 51.0 (CH), 62.8 (C), 94.1 (C), 102.0 (CH$_2$), 152.7 (C); m/z (EI) 282 (M$^+$, 100%), 267 (75).

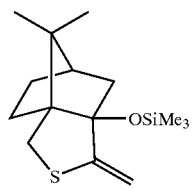

4

Epoxidation of Benzaldehyde Using Sulfides 3 and 4

To a rapidly stirred solution of sulfide, rhodium (II) acetate dimer (1 mol %, 1.5 mg, 003 mmol), benzyltriethylammonium chloride (20% mmol, 15 mg, 0066 mmol) and benzaldehyde (0.034 mL, 0.33 mmol) in anhydrous acetonitrile (1 mL) was added benzaldehyde tosyl hydrazone sodium salt (147 mg, 0.495 mmol). The mixture was stirred at 30° C. for 40 hours. The mixture was then cooled and ethyl acetate/water added. The aqueous phase was extracted with ethyl acetate and the combined organic extracts dried with sodium sulfate, filtered and concentrate in vacuo. The residue was purified on silica with 20% DCM/petrol to give the epoxide.

| Sulfide | mmol sulfide | yield (%) | e.e.(%) | trans/cys |
|---------|--------------|-----------|---------|-----------|
| 3 | 0.33 | 23 | 63 | 55/45 |
| 4 | 0.06 | 78 | 76 | 85/15 |

N,N'-Dimethyl Isopulegol Dithiocarbamate

To a solution of (−)-isopulegol (1.0 g, 6.48 mmol) in THF (10 ml) at room temperature was added sequentially triphenylphosphine (4.42 g, 2.6 eq, 16.86 mmol) and zinc N,N'-dimethyldithiocarbamate (1.98 g, 1.0 eq, 6.48 mmol). The white mixture was then cooled to 0° C. and diethyl azodicarboxylate (2.86 ml, 2.8 eq, 18.15 mmol) was added dropwise over 10 minutes. The mixture was slowly warmed to room temperature and stirred for 24 hours, after which time it was diluted with ethyl acetate (50 ml) and suction filtered through a pad of silica. Solvent removal and purification by flash column chromatography (0→2.5% v/v ethyl acetate/hexane) afforded the product as a light beige solid (1.36 g, 82%). Recrystallisation from hexane gave clear crystals; $d_H$ (250 MHz, CDCl$_3$) 4.82 (1H, obs sextet, J 1.5, CHS), 4.68–4.64 (2H, m, vinyl H), 3.54 (3H, s, NCH$_3$), 3.37 (3H, s, NCH$_3$), 2.31 (1H, br d, J 12.2, CHHS), 2.13 (1H, ddd, J 13.7, 5.5 and 3.4, CHHS), 1.90–1.63 (3H, m), 1.77 (3H, s, CH$_3$), 1.49–1.32 (2H, m), 1.11–096 (1H,m), 0.91 (3H, d, J 6.7, CH$_3$).

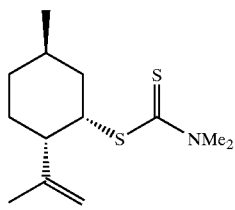

Isopulegol Thiol

To a solution of dithiocarbamate (2.69 g, 10.47 mmol) in ether (15 ml) at 0° C. was added lithium aluminium hydride (994 mg, 2.5 eq, 26.17 mmol). The mixture was warmed to room temperature and then refluxed for 24 hours. At 0° C., saturated sodium sulfate solution was cautiously added until the mixture was a white colour. This suspension was then suction filtered (ether washings, 3×30 ml). Solvent removal and purification by flash column chromatography (petrol) afforded the product as a clear oil (1.62 g, 90%); $d_H$ (250 MHz, CDCl$_3$) 4.90 (1H, m, vinyl H), 4.71 (1H, m, vinyl H), 3.63 (1H, m, CHS), 2.18–2.12 (1H, m), 1.96–1.71 (4H, m), 1.74 (3H, s, CH$_3$), 1.55–1.42 (2H, m), 1.33 (1H, obs dd, J 4.8 and 1.1), 1.04–0.84 (1H, m), 0.90 (3H, d, J 6.1, CH$_3$).

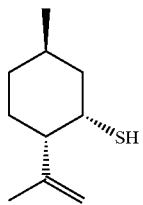

Isopulegol-derived Sulfide

A mixture of isopulegol thiol (850 mg, 5.0 mmol) and azo-bisisobutyronitrile (82 mg, 0.10 eq, 0.50 mmol) in benzene (50 ml) was refluxed under nitrogen for 15 hours. Solvent removal and purification by flash column chromatography (0.5% v/v ether/hexane) afforded the product as a clear oil (800 mg, 94%) (92:8 ratio of diastereomers); $d_H$ (250 MHz, CDCl$_3$) 3.80 (1H, br s, CHS), 2.85 (1H, dd, J 10.1 and 7.3, CHHS), 2.59 (1H, obs t, J 10.1, CHHS), 2.40–2.22 (1H, m), 1.96–1.66 (4H, m), 1.51–1.24 (4H, m), 1.02 (3H, d, J 6.7, CH$_3$), 0.87 (3H, d, J 6.4, CH$_3$).

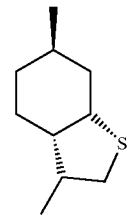

Application of this sulfide in the in situ epoxidation cycle (0.33 mmol scale, 1.0 eq benzaldehyde, 1 mol % Rh$_2$(OAc)$_4$, 20 mol % sulfide, 20 mol % BnEt$_3$N$^+$Cl$^-$, 1.5 eq benzaldehyde tosylhydrazone sodium salt, MeCN (0.33 M in PhCHO), 30–35° C., 40 hours) gave stilbene oxide as a white solid (88% yield) and as a 90:10 mixture (trans:cis) of diastereomers by $^1$H NMR and 19% ee (S,S major) by chiral GC (a-CD column, 20 psi, 180° C. isothermal).

(2R,5R)-(+)-2,5-Dimethyldithiolane

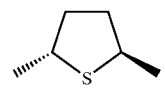

This sulfide was prepared according to the literature procedure (*Tetrahedron: Asymmetry*, 1998, 9, 189). Application of this sulfide in the in situ epoxidation cycle (conditions as shown above) gave stilbene oxide as a white solid (60% yield) and as a 90:10 mixture (trans:cis) of diastereomers by $^1$H NMR and 41% ee (S,S major) by chiral HPLC (OD column, 1% $^i$PrOH/hexane, 2 ml/min).

(R)-(+)-bis(Methylthio)-1,1'-binaphthalene

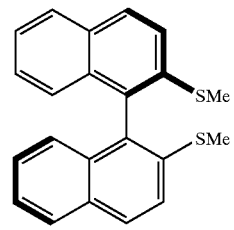

This sulfide was prepared according to the literature procedure (*J. Org. Chem.*, 1993, 58, 1748). Application of this sulfide in the in situ epoxidation cycle (conditions as shown above, except MeCN/THF (3:1) solvent mixture) gave stilbene oxide as a white solid (78% yield) and as a 95:5 mixture (trans:cis) of diastereomers by $^1$H NMR and 11% ee (R,R major) by chiral GC (a-CD column, 20 psi, 180° C. isothermal).

(1R,2S,4R,5S)-2,5-Dimethyl-thiabicyclo[2.2.1]heptane

To a solution of (+)-2,5-dimethylcyclohexane-1,4-diol bis(methanesulfonate) (prepared according to the literature procedure: *Organometallics*, 1991, 10, 3449) (1.19 g, 5.8 mmol) in DMSO (25 ml) at room temperature was added sodium sulfide (469 mg, 1.0 eq, 6.0 mmol). The green solution was heated to 120° C. for 7 hours and then cooled to room temperature overnight. The mixture was poured into a water/ice solution and extracted with pentane (3×25 ml). The combined organics were dried (MgSO$_4$), concentrated in vacuo and purified by flash column chromatography (pentane) to afford the crude product. Bulb-to-bulb distillation gave the desired sulfide (158 mg, 19%); d$_H$ (250 MHz, CDCl$_3$) 3.30 (2H, d, J 4.0), 1.77 (4H, m), 1.18 (2H, m), 0.96 (6H, d, j 6.4, 2×CH$_3$).

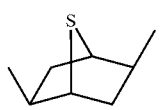

Application of this sulfide in the in situ epoxidation cycle (conditions as shown previously, except run at 22° C. and 42 hours) gave stilbene oxide as a white solid (73% yield) and as a 92:8 mixture (trans:cis) of diastereomers by $^1$H NMR and 18% ee (S,S major) by chiral GC (a-CD column, 20 psi, 180° C. isothermal).

(1S,4R,6S)-1-Methyl 4-iso-Propene 7-Thiane 10-oxa bicyclo [4.4.0] dec-8-ene

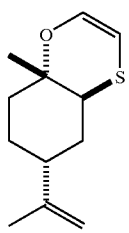

To a 60% solution in oil of NaH (0.16 g, 3.9 mmol), in DMF (7 ml) was added mercaptoacetaldehyde diethyl acetal (0.55 g, 3.7 mmol) at 0° C. Then (1R,4S)-trans-limonen-1, 2-epoxide (0.4 ml, 2.4 mmol) was added. The resulting mixture was stirred overnight at room temperature then quenched with 2N HCl and extracted with Et$_2$O. The combined extracts were washed twice with 10% NaOH and brine, dried over MgSO$_4$, filtered and the solvent was removed under vacuo. The residue was then dissolved in dry Et$_2$O (30 ml) and BF$_3$.Et$_2$O (0.9 ml, 7.2 mmol) was added at 0° C. After 3h at room temperature, the resulting mixture was quenched with a saturated solution of NH$_4$Cl, and the aqueous layer was extracted with Et$_2$O. The combined extracts were washed with brine, dried over MgSO$_4$ and the solvent was removed under vacuo after filtration. The residue was purified by chromatography through silica gel (petroleum ether/EtOAc 95:5) to afford pure diene (0.41 g, 80%) as a colourless oil.

$^1$H NMR (CDCl$_3$, δppm, J Hz): 6.42 (1H, d, J 6.5, =CHO), 4.98–4.86 (3H, m, =CH$_2$ and =CHS), 3.15 (1H, dd, J 13.3, 3.5, CHS), 2.38 (1H, m, CH), 2.15–2.07 (2H, m, 2CH), 1.77–1.70 (4H, m, CH$_2$ and CH), 1.64–1.32 (3H, m, 3CH), 1.32 (3H, s, CH$_3$). IR (film KBr) (ν$_{max}$): 3084, 2940, 2870, 1640, 1607, 1458, 1442, 1377, 1241, 1061, 1046, 890, 702 cm$^{-1}$.

(1S,4R,6S)-1-Methyl 4-iso-propyl 7-thiane 10-oxa bicyclo [4.4.0] decane

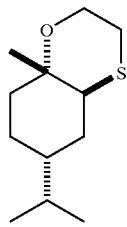

The preceding diene was dissolved in EtOH (50 ml) and a 5% PdS/C (100 mg) was added. The mixture was stirred overnight under an H$_2$ atmosphere, then filtered through celite. The residue was purified by chromatography through silica gel (petroleum ether/EtOAc 95:5) to afford pure sulfide (0.33 g, 80%) as a colourless oil.

$^1$H NMR (CDCl$_3$, δppm, J Hz): 4.01 (1H, dt, J 12.3, 2.3, CHO), 3.82–3.78 (1H, m, CHO), 3.07–3.02 (2H, m, CH$_2$S), 2.35 (1H, dt, J 13.4, 2.0, CHS), 1.94–1.16 (11H, m, and CH$_3$), 0.89 (6H, d, J 6.6, (CH$_3$)$_2$).

IR (film KBr) (ν$_{max}$): 2936, 2868, 1459, 1370, 1298, 1188, 1108, 1080, 630 cm$^{-1}$.

(2R)-2-Iso-propyl 5-methyl 3-thiane hex-5-enol

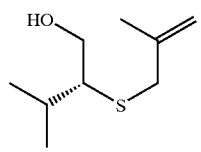

General procedure for the alkylation of the mercaptoalcohol:

To a mixture of (2R)-2-iso-propyl 1,2-mercaptoethanol (1.00 mmol) and sodium methoxide (1.13 mmol) in methanol (2 ml) was added methallyl bromide (1.00 mmol) at 0° C., and the mixture was stirred at 0° C. for 1 h and at 25° C. for 3h. Then, the solvent was removed under reduced pressure and the residue was filtered and washed with ether. The ether layer was washed with brine, dried over MgSO$_4$ and the solvent was evaporated under reduced pressure. The residue was purified by chromatography through silica gel (petroleum ether/Et$_2$O 8:2) to afford pure alkylated compound (64%) as a pale yellow oil.

$^1$H NMR (250 MHz, CDCl$_3$), δppm: 0.94–1.00 (m, 6H, (CH$_3$)$_2$CH), 1.82 (s, 3H, CH$_3$C=CH$_2$), 1.85–2.00 (m, 1H, (CH$_3$)$_2$CH), 2.18 (bs, 1H, OH), 2.48–2.55 (m, 1H, CHS), 3.06 (dd, J=13 Hz and 1 Hz, 1H, CHHS), 3.16 (dd, J=13 Hz and 1 Hz, 1H, CHHS), 3.53 (dd, J=11 Hz and 7 Hz, 1H, CHHO), 3.68 (dd, J=11 Hz and 5 Hz, 1H, CHHO), 4.80–4.84 (m, 2H, C=CH$_2$).

(5R)-2-Iodomethyl 2-methyl 5-iso-propyl 1,4-oxathiane

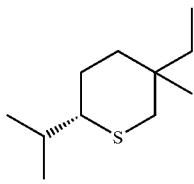

General procedure for the iodocyclisation:

To a stirred solution of the above alkylated compound (1.00 mmol) in acetonitrile (11 ml) were added anhydrous sodium carbonate (10.00 mmol) and iodine (5.00 mmol). The mixture was stirred in the dark for 8 h at room temperature, diluted with ether and then treated with a 10% aqueous solution of $Na_2SO_3$. The organic layer was separated, washed with brine, and dried over $MgSO_4$. Removal of the solvent under reduced pressure followed by chromatography of the residue through silica gel (petroleum ether/$Et_2O$ 8:2) afforded pure iodo compound (55%) as a mixture of diastereoisomers.

(5R)-2,2-Dimethyl 5-iso-propyl 1,4-oxathiane

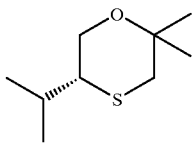

General procedure for the reduction:

To a cooled solution of lithium aluminium hydride (1.00 mmol) in THF (2 ml) was added dropwise a solution of the iodo compound (1.00 mmol) in THF (3 ml). At the end of the addition, the ice bath was removed and the mixture was stirred overnight. The mixture was then recooled to 0° C. and treated with a saturated solution of $NH_4Cl$ and diluted HCl until the entire solid was dissolved. The aqueous layer was extracted with $Et_2O$. The combined extracts were washed with brine, dried over $MgSO_4$ and the solvents were evaporated in vacuo. The residue was purified by chromatography through silica gel (petroleum ether/$Et_2O$ 7:3) to afford pure sulfide (64%) as a pale yellow liquid.

$^1$H NMR (250 MHz, $CDCl_3$), δppm: 0.96 (d, J=6 Hz, 3H, $CH_3CH$), 0.98 (d, J=6 Hz, 3H, $CH_3CH$), 1.25 (s, 3H, $CH_3C$), 1.35 (s, 3H, $CH_3C$), 1.67–1.80 (m, 1H, $CH_3CH$), 2.35 (d, J=13 Hz, 1H, CHHS), 2.55 (ddd, J=10 Hz, 6 Hz and 3 Hz, 1H, CHS), 2.71 (d, J=13 Hz, 1H, CHHS), 3.71 (dd, J=12 Hz and 10 Hz, 1H, CHHO), 3.86 (dd, J=12 Hz and 3 Hz, 1H, CHHO).

(2R)-2,5-Dimethyl 3-thiane hex-5-enol

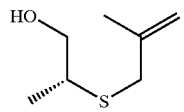

Following the general procedure for the alkylation of the mercaptoalcohol, (2R)-2-methyl 1,2-mercaptoethanol gave 72% of pure alkylated compound.

$^1$H NMR (250 MHz, $CDCl_3$), δppm: 1.24 (d, J=7 Hz, 3H, $CH_3CH$), 1.81 (s, 3H, $CH_3C=CH_2$), 2.15 (bs, 1H, OH), 2.75–2.88 (m, 1H, CHS), 3.07 (dd, J=14 Hz and 1Hz, 1H, CHHS), 3.18 (dd, J=14 Hz and 1 Hz, 1H, CHHS), 3.47 (dd, J=11 Hz and 6 Hz, 1H, CHHO), 3.59 (dd, J=11 Hz and 5 Hz, 1H, CHHO), 4.81–4.84 (m, 2H, C=$CH_2$).

(5R)-2-Iodomethyl 2,5-dimethyl 1,4-oxathiane

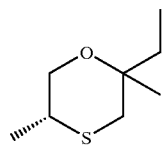

Following the general procedure for the iodocyclisation, the preceding compound gave 45% of a mixture of diastereoisomers.

(5R)-2,2,5-Trimethyl 1,4-oxathiane

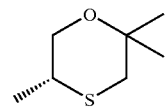

Reduction of the preceding iodo compound, following the general procedure, gave 45% of pure sulfide.

$^1$H NMR (250 MHz, $CDCl_3$), δppm: 1.13 (d, J=7 Hz, 3H, $CH_3CH$), 1.39 (s, 3H, $CH_3C$), 1.48 (s, 3H, $CH_3C$), 2.40 (d, J=13 Hz, 1H, CHHS), 2.80–3.00 (m, 2H, CHS and CHHS), 3.57 (dd, J=12 Hz and 10 Hz, 1H, CHHO), 3.92 (dd, J=12 Hz and 3 Hz, 1H, CHHO).

CHEMICAL FORMULAE
(AS IN DESCRIPTION)

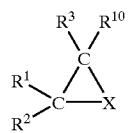

(I)

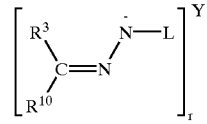

(II)

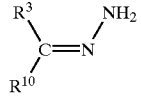

(IIa)

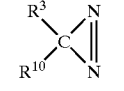

(IIb)

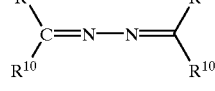

(IIc)

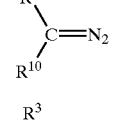

(III)

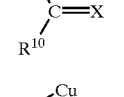

(IV)

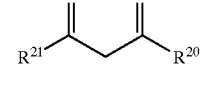

(V)

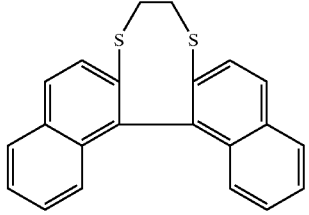

(A)

-continued
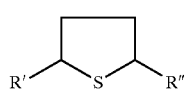 (B)
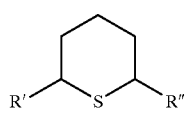 (C)
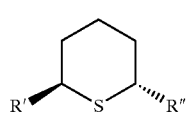 (C')
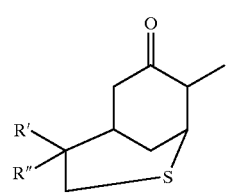 (F)
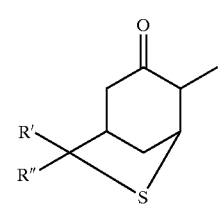 (G)
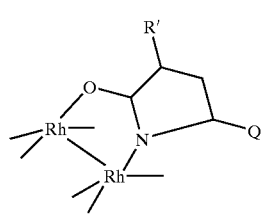 (H)
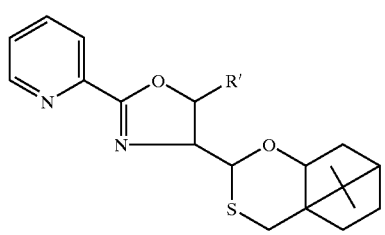 (J)
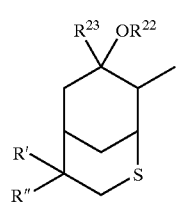 (K)
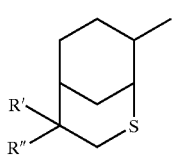 (L)
-continued
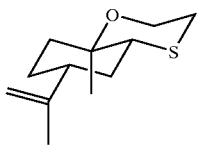 (M)
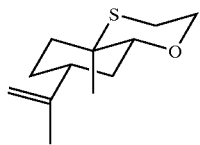 (N)
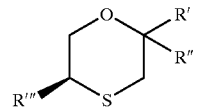 (O)
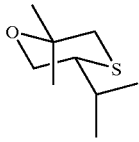 (O'')
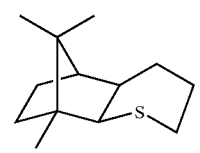 (P)
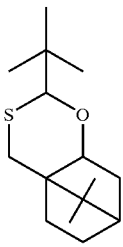 (Q)
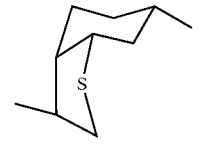 (R)
 (S)
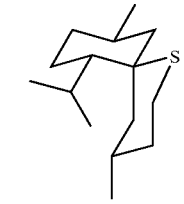 (T)

-continued (U) 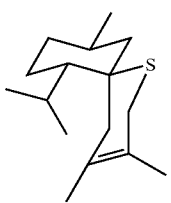

(V) 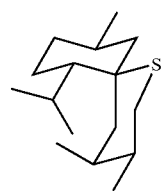

(W) 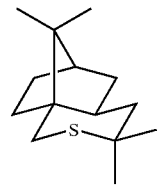

(X) 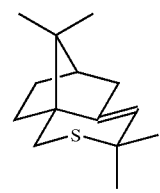

(Y) 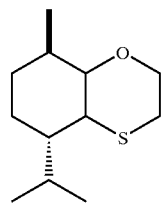

(Z) 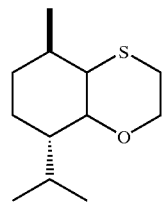

(AA) 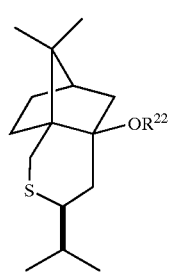

-continued (AB) 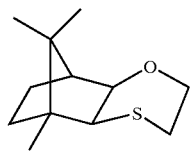

What is claimed is:

1. A process for the preparation of an oxirane, aziridine or cyclopropane of formula (I),

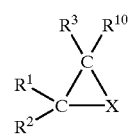
(I)

wherein X is oxygen, $NR^4$ or $CHR^5$, $R^1$ is hydrogen, alkyl, aryl, heteroaromatic, heterocyclic or cycloalkyl; $R^2$ is hydrogen, alkyl, aryl, heteroaromatic, $CO_2R^8$, $CHR^{14}NHR^{13}$, heterocyclic or cycloalkyl; or $R^1$ and $R^2$ join together to form a cycloalkyl ring; $R^3$ and $R^{10}$ are, independently, hydrogen, alkyl, aryl, heteroaromatic, $CO_2R^8$, $R^8_3Sn$, $CONR^8R^9$, trialkylsilyl or triarylsilyl; $R^4$ is an electron withdrawing group; $R^5$ is alkyl, cycloalkyl, aryl, heteroaromatic, $SO_2R^8$, $SO_3R^8$, $COR^8$, $CO_2R^8$, $CONR^8R^9$, $PO(R^8)_2$, $PO(OR^8)_2$ or CN; $R^8$ and $R^9$ are independently alkyl or aryl; and $R^{13}$ and $R^{14}$ are independently hydrogen, alkyl or aryl; the process comprising the steps of (a) degrading in situ a compound of formula (II), (IIa), (IIb) or (IIc):

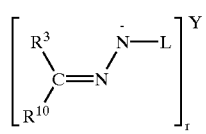
(II)

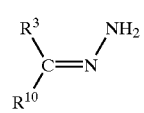
(IIa)

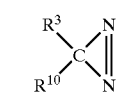
(IIb)

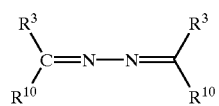
(IIc)

wherein $R^3$ and $R^{10}$ are as defined above; Y is a cation; depending on the nature of Y, r is 1 or 2; and L is a suitable leaving group, to form a diazo compound of formula (III):

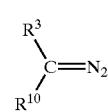
(III)

wherein $R^3$ and $R^{10}$ are as defined above;

(b) reacting the compound of formula (III) with a suitable transition metal catalyst;

(c) reacting the product of step (b) with a sulphide of formula $SR^6R^7$, wherein $R^6$ and $R^7$ are independently alkyl, aryl or heteroaromatic, or $R^6$ and $R^7$ join together to form an optionally substituted ring which optionally includes an additional heteroatom; and (d) reacting the product of step (c) with a compound of formula (IV):

(IV)

wherein $R^1$ and $R^2$ are as defined above.

2. A process according to claim 1, wherein a compound of formula (II) is thermally decomposed in the presence of an aprotic solvent and a phase transfer catalyst, but in the absence of free base.

3. A process according to claim 1, wherein the sulphide is a cyclic sulphide.

4. A process according to claim 1, wherein the sulphide has the formula (VI):

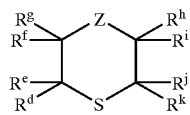

wherein Z represents —$CH_2$—, O, S, —CHalkyl—, $C(alkyl)_2$—, or $NR^4$, each of $R^{d-k}$ independently represents H, alkyl or alkoxyalkyl or are linked to form a cyclic moiety, provided that at least 2 of $R^d$, $R^e$, $R^j$ and $R^k$ represent H, and $R^4$ is $SO_2R^8$, $SO_3R^8$, $COR^8$, $CO_2R^8$, $CONR^8R^9$, $PO(R^8)_2$, $PO(OR^8)_2$ or CN, and $R^8$ and $R^9$ are independently alkyl or aryl.

5. A process according to claim 4, wherein Z represents O.

6. A compound of formula (VII):

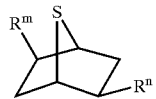

wherein $R^m$ and $R^n$ are each independently alkyl or alkoxyalkyl.

7. A process according to claim 2, wherein the sulphide is a cyclic sulphide.

8. A process according to claim 7, wherein the sulphide has the formula (VI):

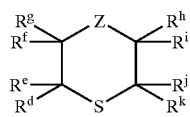

wherein Z represents —$CH_2$—, O, S, —CHalkyl—, $C(alkyl)_2$— or $NR^4$, each of $R^{d-k}$ independently represents H, alkyl or alkoxyalkyl or are linked to form a cyclic moiety, provided that at least 2 of $R^d$, $R^e$, $R^j$ and $R^k$ represent H, and $R^4$ is $SO_2R^8$, $SO_3R^8$, $COR^8$, $CO_2R^8$, $CONR^8R^9$, $PO(R^8)_2$, $PO(OR^8)_2$ or CN, and $R^8$ and $R^9$ are independently alkyl or aryl.

9. A process according to claim 8, wherein Z represents O.

10. A process according to one of claims 1–5 or claims 7–9, wherein in the compound of formula (IV), X is O, $R^1$ is H and $R^2$ is an optionally substituted alkyl group comprising from 1 to 10 carbon atoms; an optionally substituted phenyl group, or an optionally substituted heteroaromatic group comprising a 5 or 6 membered ring.

11. A process according to any one of claims 1 to 5 or claims 7–9, wherein in the compound of formula (IV) is a ketone, and $R^1$ and $R^2$ are selected such that:

a) at least one of $R^1$ and $R^2$ represents an optionally substituted alkyl group comprising from 1 to 10 carbon atoms, at least one alkyl carbon alpha to the keto group carrying at least one hydrogen atom;

b) $R^1$ and $R^2$ together form a cycloalkyl group at least one alkyl carbon alpha to the keto group carrying at least one hydrogen atom; or c) at least one $R^1$ and $R^2$ represents an aryl or heteroaromatic group, the ring positions adjacent to the keto group carrying hydrogen atoms.

12. A process according to any one of claims 1 to 5 or claims 7–9, wherein in the compound of formula (IV) is an alkene in which the carbon-carbon double bond is conjugated with an electron withdrawing group.

13. A process according to any one of claims 1 to 5 or claims 7–9, wherein in the compound of formula (IV) is an imine in which one of $R^1$ and $R^2$ represents H, alkyl, phenyl or a heteroaromatic group, the other representing alkyl, aryl or a heteroaromatic group, wherein any alkyl group preferably comprises from 1 to 10 carbon atoms; and is optionally substituted; any phenyl group is optionally substituted, any heteroaromatic group comprises a 5 or 6 membered ring and $R^4$ is $SO_2R^8$, $SO_3R^8$, $COR^8$, $CO_2R^8$, $CONR^8R^9$, $PO(R^8)_2$, $PO(OR^8)_2$ or CN, wherein $R^8$ and $R^9$ are independently alkyl or aryl.

14. A process according to one of claims 1–5 or claims 7–9, wherein the sulphide is an aliphatic sulphide.

15. A process according to one of claims 1–5 or claims 7–9, wherein the transition metal catalyst is a rhodium, ruthenium, copper, nickel or palladium compound, preferably a rhodium (II), ruthenium (II), copper (I) or (II), nickel (II) compound or palladium (II) compound.

16. A process for the generation of diazo compounds, wherein a compound of formula II

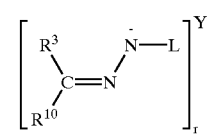

(II)

is thermally decomposed in the presence of an aprotic solvent and a phase transfer catalyst, but in the absence of free base, wherein:

$R^3$ and $R^{10}$ are independently hydrogen, alkyl, aryl, heteroaromatic, $CO_2R^8$, $R^8{}_3Sn$, $CONR^8R^9$, trialkylsilyl or triarylsilyl;

Y is a cation;

depending on the nature of Y, r is 1 or 2; and

L is a suitable leaving group.

17. A process according to claim 16, wherein the process is carried out under anhydrous conditions.

18. A process according to either of claims 16 or 17, wherein the compound of formula II is substantially insoluble in the aprotic solvent, and is employed as a suspension.

19. A process according to any one of claims 16 or 17, wherein the compound of formula II is a sodium salt.

20. A compound having the chemical formula (VI):

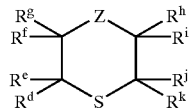

wherein Z represents —$CH_2$—, O, S, —CHalkyl—, C(alkyl)$_2$— or NR$^4$, each of R$^{d-k}$ independently represents H, alkyl or alkoxyalkyl or are linked to form a cyclic moiety, provided that at least 2 of R$^d$, R$^e$, R$^j$ and R$^k$ represent H; R$^4$ is an electron withdrawing group and either R$^d$ and R$^e$ or R$^j$ and R$^k$ are linked to form a cyclic group.

21. A compound having the chemical formula (VI):

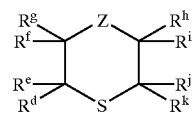

wherein Z represents O and wherein both of R$^f$ and R$^g$ and one of R$^d$ and R$^e$ are independently alkyl or alkoxyalkyl, with the remainder of R$^{d-k}$ representing hydrogen.

22. A compound according to claim 6 wherein R$^m$ and R$^n$ are each independently C$_{1-6}$alkyl or C$_{1-4}$alkoxyC$_{1-6}$alkyl.

* * * * *